US011802759B2

(12) United States Patent
Swanson

(10) Patent No.: US 11,802,759 B2
(45) Date of Patent: Oct. 31, 2023

(54) INTEGRATED PHOTONIC CHIP WITH COHERENT RECEIVER AND VARIABLE OPTICAL DELAY FOR IMAGING, SENSING, AND RANGING APPLICATIONS

(71) Applicant: Eric Swanson, Gloucester, MA (US)

(72) Inventor: Eric Swanson, Gloucester, MA (US)

(*) Notice: Subject to any disclaimer, the term of this patent is extended or adjusted under 35 U.S.C. 154(b) by 0 days.

(21) Appl. No.: 17/221,835

(22) Filed: Apr. 4, 2021

(65) Prior Publication Data
US 2021/0356249 A1    Nov. 18, 2021

Related U.S. Application Data

(60) Provisional application No. 63/024,569, filed on May 14, 2020, provisional application No. 63/024,478, filed on May 13, 2020.

(51) Int. Cl.
*G01B 9/02* (2022.01)
*G01B 9/02091* (2022.01)
(Continued)

(52) U.S. Cl.
CPC ..... *G01B 9/02091* (2013.01); *G01B 9/02004* (2013.01); *G01B 9/02011* (2013.01);
(Continued)

(58) Field of Classification Search
CPC ............ G01B 9/02091; G01B 9/02004; G01B 9/02011; G01B 9/02015; G01B 9/02067; G06T 11/005; G06T 11/008
See application file for complete search history.

(56) References Cited

U.S. PATENT DOCUMENTS 5,212,743 A    5/1993    Heisman
5,321,501 A    6/1994    Swanson
(Continued)

FOREIGN PATENT DOCUMENTS

EP    0981733    11/2004
EP    0883793    11/2007
(Continued)

OTHER PUBLICATIONS

Xingchen Ji, Xinwen Yao, Yu Gan, Aseema Mohanty, Mohammad A. Tadayon, Christine P. Hendon, and Michal Lipson , "On-chip tunable photonic delay line", APL Photonics 4, 090803 (2019) https://doi.org/10.1063/1.5111164 (Year: 2019).*
(Continued)

*Primary Examiner* — Uzma Alam
*Assistant Examiner* — Jonathon Cook
(74) *Attorney, Agent, or Firm* — Rauschenbach Patent Law Group, PLLC; Kurt Rauschenbach

(57) ABSTRACT

An interferometric measurement system includes ports configured to receive an optical signal from an optical source and an optical signal from a target. A photonic integrated circuit includes a variable delay configured to select between at least two optical paths from the input to an output such that the optical signal from the optical source passes to the output while experiencing an optical delay based on a selected one of the at least two optical paths where a loss of the optical signal from the optical source provided to the input that passes to the output is nominally the same for each of the at least two optical paths. An optical receiver is configured to receive the optical signal from the target and to receive the optical signal from the optical source that experiences the optical delay based on the selected one of the at least two optical paths and generates a corresponding electrical receive signal at an electrical output. A processor (Continued)

is configured to generate an interferometric measurement signal based on the receive signal.

31 Claims, 10 Drawing Sheets

(51) Int. Cl.
| | |
|---|---|
| *G01B 9/02001* | (2022.01) |
| *G01B 9/02055* | (2022.01) |
| *G06T 11/00* | (2006.01) |
| *G01B 9/02004* | (2022.01) |
| *G01B 9/02015* | (2022.01) |

(52) U.S. Cl.
CPC ..... *G01B 9/02015* (2013.01); *G01B 9/02067* (2013.01); *G06T 11/005* (2013.01); *G06T 11/008* (2013.01)

(56) References Cited

U.S. PATENT DOCUMENTS

| | | | |
|---|---|---|---|
| 5,459,570 | A | 10/1995 | Swanson |
| 5,465,147 | A | 11/1995 | Swanson |
| 5,956,355 | A | 9/1999 | Swanson |
| 6,134,003 | A | 10/2000 | Tearney |
| 6,160,826 | A | 12/2000 | Swanson |
| 6,191,862 | B1 | 2/2001 | Swanson |
| 6,288,784 | B1 | 10/2001 | Hitzenberger |
| 6,445,939 | B1 | 9/2002 | Swanson |
| 6,485,413 | B1 | 11/2002 | Boppart |
| 6,501,551 | B1 | 12/2002 | Tearney |
| 6,564,087 | B1 | 5/2003 | Pitris |
| 6,891,984 | B2 | 5/2005 | Peterson |
| 7,061,618 | B2 | 6/2006 | Atia et al. |
| 7,530,948 | B2 | 5/2009 | Seibel |
| 7,843,572 | B2 | 11/2010 | Tearney et al. |
| 7,864,822 | B2 | 1/2011 | Bouma |
| 7,916,387 | B2 | 3/2011 | Schmitt |
| 8,078,245 | B2 | 12/2011 | Daly |
| 8,384,909 | B2 | 2/2013 | Yun |
| 8,416,818 | B2 | 4/2013 | Bouma |
| 8,437,007 | B2 | 5/2013 | Flanders |
| 8,515,221 | B2 | 8/2013 | Flanders |
| 8,690,330 | B2 | 4/2014 | Hacker et al. |
| 8,711,364 | B2 | 4/2014 | Brennan |
| 8,854,629 | B2 | 10/2014 | Frisken |
| 8,947,648 | B2 | 2/2015 | Swanson |
| 8,994,954 | B2 | 3/2015 | Minneman |
| 9,008,142 | B2 | 4/2015 | Minneman |
| 9,044,164 | B2 | 6/2015 | Hacker et al. |
| 9,162,404 | B2 | 10/2015 | Doerr |
| 9,400,169 | B2 | 7/2016 | Zhou |
| 9,464,883 | B2 | 10/2016 | Swanson et al. |
| 9,683,928 | B2 | 6/2017 | Swanson |
| 10,107,616 | B2 | 10/2018 | Zhou |
| 10,126,572 | B2 | 11/2018 | Zhang et al. |
| 10,132,610 | B2 | 11/2018 | Swanson et al. |
| 10,191,145 | B2 | 1/2019 | Swanson |
| 10,401,883 | B2 | 9/2019 | Swanson et al. |
| 10,416,288 | B2 | 9/2019 | Swanson |
| 10,895,525 | B2 | 1/2021 | Swanson |
| 10,907,951 | B2* | 2/2021 | Avci ............... G01B 9/02051 |
| 10,969,571 | B2 | 4/2021 | Swanson |
| 2006/0187537 | A1 | 8/2006 | Huber et al. |
| 2011/0218404 | A1 | 9/2011 | Hirakawa |
| 2012/0002971 | A1 | 1/2012 | Doerr |
| 2012/0099112 | A1 | 4/2012 | Alphonse et al. |
| 2012/0224165 | A1 | 9/2012 | Swanson |
| 2012/0226118 | A1 | 9/2012 | Delbeke et al. |
| 2013/0044974 | A1* | 2/2013 | Doerr ............... G02F 1/225 385/3 |
| 2013/0209022 | A1 | 8/2013 | Doerr |
| 2014/0125983 | A1* | 5/2014 | Nitkowski ......... G01J 3/4531 356/450 |
| 2014/0126902 | A1 | 5/2014 | Swanson |
| 2014/0126990 | A1 | 5/2014 | Swanson |
| 2014/0147079 | A1 | 5/2014 | Doerr |
| 2014/0160488 | A1 | 6/2014 | Zhou |
| 2014/0235948 | A1 | 8/2014 | Mahalati et al. |
| 2014/0376000 | A1 | 9/2014 | Swanson |
| 2014/0376001 | A1 | 12/2014 | Swanson |
| 2016/0231101 | A1 | 8/2016 | Swanson et al. |
| 2016/0357007 | A1 | 12/2016 | Swanson |
| 2017/0143196 | A1 | 5/2017 | Liang et al. |
| 2017/0205253 | A1 | 7/2017 | Handerek |
| 2017/0227399 | A1* | 8/2017 | Hu ............... G02F 1/3136 |
| 2019/0049300 | A1* | 2/2019 | Gu ............... G01J 3/44 |

FOREIGN PATENT DOCUMENTS

| | | |
|---|---|---|
| EP | 1839375 | 4/2014 |
| WO | 2012088361 | 6/2012 |
| WO | 2014/088650 | 6/2014 |
| WO | 2014/089504 | 6/2014 |

OTHER PUBLICATIONS

C. Boudoux, et al., Rapid wavelength-swept spectrally encoded confocal microscopy, Optics Express, Oct. 3, 2005, pp. 8214-8221, vol. 13, No. 20, OSA.

Dongyao Cui, et al., Multifiber angular compounding optical coherence tomography for speckle reduction, Optics Letter, Jan. 1, 2017, pp. 125-128, vol. 42, No. 1, Optical Society of America.

Daniel J. Fechtig, et al., Line-field parallel swept source MHz OCT for structural and functional retinal imaging, Biomedical Optics Express, Mar. 1, 2015, pp. 716-735, vol. 6, No. 3, OSA.

Simon Lemire-Renaud, et al., Double-clad fiber coupler for endoscopy, Optics Express, May 10, 2020, 9755-9764, vol. 18, No. 10, OSA.

Florence Rossant, et al., Highlighting directional reflectance properties of retinal substructures from D-OCT images, IEE Transactions on Biomedical Engineering, Nov. 2019, pp. 3105-3118, vol. 66, No. 11, EMB.

Seen Young Ryu, et al., Combined system of optical coherence tomography and fluorescence spectroscopy based on double-cladding fiber, Optics Letters, pp. 2347-2349, Oct. 15, 2008, vol. 33, No. 20.

Juan Sancho-Dura, et al., Handheld multi-modal imaging for point-of-care skin diagnosis based on akinetic integrated optics optical coherence tomography, Biophotonics Journal, 2018, pp. 1-6, 2018, Wiley-VCH Verlag, GmbH & Co. KGaA Weinheim.

Tuqiang Xie, et al., Fiber-optic-bundle-based optical coherence tomography, Optics Letters, Jul. 15, 2005, pp. 1803-1805, vol. 30, No. 14.

Gunay Yurtsever, et al., Photonic integrated Mach-Zehnder interferometer with an on-chip reference arm for optical coherence tomography, Biomedical Optics Express, Apr. 1, 2014, pp. 1050-1060, vol. 5, No. 4, OSA.

Chao Zhou, et al., Space-division multiplexing optical coherence tomography, Optics Express, Aug. 12, 2013, pp. 19219-19227, vol. 21, No. 16, OSA.

Chao Zhou, et al., Space-division multiplexing optical coherence tomography, Optics Express, Aug. 6, 2013, pp. 19219-19227 vol. 21, No. 16, DOI:10.1364/OE.21.019219.

Yongyan Huang, et al., Wide-field high-speed space-division multiplexing optical coherence tomography using an integrated photonic device, Biomedical Optics Express, Jul. 28, 2017, pp. 3856-3867, vol. 8, No. 8, DOI:10.1364/BOE.8.003856.

Amir Porat, Ori Katz, Esben Ravn Andresen, Herve Rigneault, Dan Oron, Sylvain Gigan, "Widefield Lensless Endoscopy via Speckle Correlations", Optics and Photonics News, Dec. 2016, p. 41.

Martin Ploschner, Tomas Tyc and Tomas Ciamar, "Seeing through chaos in multimode fibres", Nature Photonics, doi: 10:1038/NPHOTON.2015, Jul. 2015,112, pp. 529-538.

Fomas Cizmár and Kishan Dholakia, "Exploiting multimode waveguides for pure fibre-based imaging" Nature Communications, 3:1027, doi: 10.1038/ncomms2024, May 2012.

(56) References Cited

OTHER PUBLICATIONS

Martin Ploschner, Branislav Straka, Kishan Dholakia and Tomas Cizmar, "Fibre-based imaging: new challenges", Adaptive Optics and Wavefront Control for Biological Systems, Proc. of SPIE vol. 9335, 93350H, doi: 10.1117/12.2077693, Mar. 2015.

M. Ploschner, B. Straka, K. Dholakia, and T. Cizmar, "GPU accelerated toolbox for real-time beam-shaping in multimode fibres", Optics Express, 2014, vol. 22, No. 3, doi:10.1364/OE.22.002933.

Miguel A. Preciado, Michael Mazilu, Kishan Dholakia, "Multimode fibre correction for applications in optomechanics using a digital micromirror device", FTu1A.6, FiO/LS, OSA 2014.

Miguel A. Preciado, Kishan Dholakia, Michael Mazilu, "Real-time optical eigenmode characterization", FTh3G.5, FiO/LS, OSA 2014.

Reza Nasiri, Mahalati, Ruo, Yu Gu, and Joseph M. Kahn, "Resolution limits for imaging through multi-mode fiber", Optics Express, Jan. 2013, vol. 21, No. 1.

S. G. Adie, N. D. Shemonski, T. S. Ralston, P. S. Carney, S. A. Boppart, "Interferometric Synthetic Aperture Microscopy (ISAM)", in Optical Coherence Tomography: Technology and Applications. 2nd ed.; Drexler, W., Fujimoto, J. G., Eds.; Springer International Publishing, Switzerland, 2015, 965-1004, 2015.

Y. Xu, Y. Z. Liu, S. A. Boppart, P. S. Carney, "Automated Interferometric Synthetic Aperture Microscopy and Computational Adaptive Optics for Improved Optical Coherence Tomography", Applied Optics, 55, (8), 2034-2041, doi:10.1364/Ao.55.002034, 2016.

F. A. South, Y. Z. Liu, Y. Xu, N. D. Shemonski, P. S. Carney, S. A. Boppart, "Polarization-Sensitive Interferometric Synthetic Aperture Microscopy", Applied Physics Letters, 107, (21), DOI: Artn 211106 10.1063/1.4936236, 2015.

Aleksandar Lukic, Sebastian Dochow, Hyeonsoo Bae, Gregor Matz, Ines Latka, Bernhard Messerschmidt, Michael Schmitt, and Jürgen Popp, "Endoscopic fiber probe for nonlinear spectroscopic imaging", Optica, vol. 4, No. 5, doi:10.1364/OPTICA.4.000496, 2017.

Ruo Yu Gu, Reza Nasiri Mahalati, and Joseph M. Kahn, "Design of flexible multi-mode fiber endoscope", Optics Express, Oct. 2015,vol. 23, No. 21, doi:10.1364/OE.23.026905.

C. Bellanger, A. Brignon, J. Colineau, and J. P. Huignard, "Coherent fiber combining by digital holography", Optics Letters, Dec. 2008, vol. 33, No. 24.

Tomas Cizmar, "Exploiting multimode waveguides for in vivo imaging" SPIE Newsroom, http://www.spie.org/newsroom/6106-exploiting-multimode-waveguides-for-in-vivo-imaging, Sep. 2015.

Yuan-Zhi Liu, F. A. South, Y. Xu, P. S. Carney, and S. A. Boppart, "Computational optical coherence tomography", https://doi.org/10.1364/BOE.8.001549, Feb. 2017.

David B. Cole, Cheryl Sorace-Agaskar, Michele Moresco, Gerald Leake, Douglas Goolbaugh, and Michel R. Watts, "Integrated heterodyne interferometer with on-chip modulators and detectors", Optics Letters, vol. 40, No. 13, Jul. 1, 2015.

Chao Zuo, Jiasong Sun, Jiaji Li, Qian Chen, "Computational microscopy with programmable illumination and coded aperture", Proceedings of the SPIE, vol. 10250, doi: 10.1117/12.2266652, 2016.

Ioannis N. Papadopoulos, Salma Farahi, Christophe Moser, and Demetri Psaltis, "High-resolution, lensless endoscope based on digital scanning through a multimode optical fiber", Biomedical Optics Express, V. 4, No. 3. 2013.

Jason P. Moore and Matthew D. Rogge, "Shape sensing using multi-core fiber optic cable and parametric curve solutions", Optics Express, vol. 20, Issue 3, pp. 2967-2973, https://doi.org/10.1364/OE.20.002967, 2012.

Paul S. Westbrook, Tristan Kremp, Kenneth S. Feder, Wing Ko, Eric. M. Monberg, Hongchao Wu, Debra A. Simoff, Thierry F. Taunay, Roy. M. Ortiz , "Continuous multicore optical fiber grating arrays for distributed sensing applications", Journal of Lightwave Technology, v PP. Issue 99, pp. 1-5, doi:10.1109/JLT.2017.2661680, 2017.

Aleksandar Lukic, Sebastian Dochow, Hyeonsoo Bae, Gregor Matz, Ines Latka, Bernhard Messerschmidt, Michael Schmitt, and Jürgen Popp, "Endoscopic fiber probe for nonlinear spectroscopic imaging", Optica, v 4, No. 5, https://doi.org/10.1364/OPTICA.4.000496, 2017.

J. Carpenter, B. J. Eggleton, and J. Schröder, "110×110 optical mode transfer matrix inversion", Opt. Express, vol. 22, pp. 96-101, 2014.

Joel Carpenter, "Everything you always wanted to know about Multimode Fiber", IEEE Photonics Society Newsletter, pp. 4-10, Aug. 2017.

Youngwoon Choi, Changhyeong Yoon Moonseok Kim Taeseok Daniel Yang Christopher Fang-Yen, Ramachandra R. Dasari, Kyoung Jin Lee, and Wonshik Choi, "Scanner-Free and Wide-Field Endoscopic Imaging by Using a Single Multimode Optical Fiber" Physical Review Letters, vol. 109, 203901, Nov. 2012.

Silvio Bianchi and Roberto Di Leonardo, "A multi-mode fiber probe for holographic micromanipulation and microscopy", Lab on a Chip, V. 121, 635, 2012.

T. S. Ralston, D. L. Marks, P. S. Carney, S. A. Boppart, "Interferometric synthetic aperture microscopy". Nature Physics, 3, (2), 129-134, 2007.

J. Carpenter, B. J. Eggleton, and J. Schröder, "Observation of Eisenbud-Wigner-Smith states as principal modes in multimode fibre," Nat Phot., vol. 9, No. 11, pp. 751-757, Nov. 2015.

J. Carpenter, B. J. Eggleton, and J. Schröder, "Comparison of principal modes and spatial eigenmodes in multimode optical fibre," Laser Photon. Rev., Dec. 2016.

J. Carpenter, B. J. Eggleton, and J. Schröder, "First demonstration of principal modes in a multimode fibre," in European Conference on Optical Communication, ECOC, 2014.

S. Fan and J. M. Kahn, "Principal modes in multimode waveguides," Opt. Lett, vol. 30, pp. 135-137, 2005.

J. Carpenter, B. J. Eggleton, and J. Schröder, "Complete spatiotemporal characterization and optical transfer matrix inversion of a 420 mode fiber," Opt. Lett., vol. 41, No. 23, pp. 5580-5583, 2016.

Bo Shuang, Wenxiao Wang, Hao She, Lawrence J. Tauzin, Charlotte Flateb, Jianbo Chen, Nicholas A. Moring, Logan D. C. Bishop, Kevin F. Kelly & Christy F. Landes, "Generalized recovery algorithm for 3D super-resolution microscopy using rotating point spread Functions", Scientific Reports, 6:30826, DOI: 10.1038/srep30826, 2016.

Ioannis N. Papadopoulos, Salma Farahi, Christophe Moser, and Demetri Psaltis, "Focusing and scanning light through a multimode optical fiber using digital phase conjugation", Optics Express, V. 20, No. 10, 2012.

A. M. Caravaca-Aguirre, E. Niv, and R. Piestun, "High-speed phase modulation for multimode fiber endoscope," Imaging Appl. Opt. (2014).

R. Y. Gu, R. N. Mahalati, and J. M. Kahn, "Noise-reduction algorithms for optimization-based imaging through multi-mode fiber," Opt. Express 22(12), 15118-15132 (2014).

D. Loterie, S. Farahi, I. Papadopoulos, A. Goy, D. Psaltis, and C. Moser, "Digital confocal microscopy through a multimode fiber," http://arxiv.org/abs/1502.04172 (2015).

E. E. Morales-Delgado, S. Farahi, I. N. Papadopoulos, D. Psaltis, and C. Moser, "Delivery of focused short pulses through a multimode fiber", Opt. Express 23(7), 9109-9120 (2015).

Y. Choi, C. Yoon, M. Kim, W. Choi, and W. Choi, "Optical imaging with the use of a scattering lens", IEEE J. Sel. Top. Quantum Electron. 20(2), 61-73 (2014).

S. Bianchi, V. P. Rajamanickam, L. Ferrara, E. Di Fabrizio, R. Di Leonardo, and C. Liberale, "High numerical aperture imaging by using multimode fibers with micro-fabricated optics", in CLEO: Science and Innovations (OSA, 2014), paper SM2N.6.

M. Plöschner and T. Čižmár, "Compact multimode fiber beam-shaping system based on GPU accelerated digital holography", Opt. Lett. 40(2), 197-200 (2015).

A. M. Caravaca Aguirre and R. Piestun, "Robustness of multimode fiber focusing through wavefront shaping", in Latin America Optics and Photonics Conference (2014).

S. Farahi, D. Ziegler, I. N. Papadopoulos, D. Psaltis, and C. Moser, "Dynamic bending compensation while focusing through a multimode fiber", Opt. Express 21(19), 22504 22514 (2013).

(56) References Cited

OTHER PUBLICATIONS

R. A. Panicker and J. M. Kahn, "Algorithms for compensation of multimode fiber dispersion using adaptive optics", J. Lightwave Technol. 27(24), 5790-5799 (2009).
R. A. Horn, Matrix Analysis, 2nd ed. (Cambridge University, 2013).
24. M. Sasaki, T. Ando, S. Nogawa, and K. Hane, "Direct photolithography on optical fiber end", Jpn. J. Appl. Phys. 41 (Part 1, No. 6B), 4350-4355 (2002).
Antonio M. Caravaca-Aguirre, Eyal Niv, Donald B. Conkey, and Rafael Piestun, "Real-time resilient focusing through a bending multimode fiber", Optics Express, vol. 21, No. 10, DOI:10.1364/OE.21.012881, (2013).
Paul H. Beckwith, Ian McMichael, and Pochi Yeh, "Image distortion in multimode fibers and restoration by polarization-preserving phase conjugation", Optics Letters, vol. 12, No. 8, 1987.
D. Z. Anderson, M. A. Bolshtyansky and B. Ya. Zel'dovich, "Stabilization of the speckle pattern of a multimode fiber undergoing bending", Optics Letters, vol. 21, No. 11, Jun. 1996.
Ami Yaacobi, Jie Sun, Michele Moresco, Gerald Leake, Douglas Coolbaugh, and Michael R. Watt, "Integrated phased array for wide-angle beam steering", Opt. Lett. 39, 4575, doi: 10.1364/OL.39.004575, 2014.
Christopher V. Poulton, Matthew J. Byrd, Manan Raval, Zhan Su, Nanxi Li, Erman Timurdogan, Douglas Coolbaugh, Diedrik Vermeulen, and Michael R. Watts, "Large-scale silicon nitride nanophotonic phased arrays at infrared and visible wavelengths", Optics Letters, v. 42, No. 1, doi: 10.1364/OL.42.000021, 2017.
Christopher V. Poulton, Ami Yaccobi, Zhan Su, Matthew J. Byrd, and Michael R. Watts, "Optical Phased Array with Small Spot Size, High Steering Range and Grouped Cascaded Phase Shifters", Advanced Photonics 2016, OSA technical Digest, paper IW1B.2, doi: 10.1364/IPRSN.2016.IW1B.2, 2016.
Manan Raval, Ami Yaacobi, Daniel Coleman, Nicholas M. Fahrenkopf, Christopher Baiocco, Gerald Leake, Thomas N. Adam, Douglas Coolbaugh, and Michael R. Watts, "Nanophotonic Phased Array for Visible Light Image Projection", in IEEE Photonics Conference (2016), paper MG3.4, doi: 10.1109/IPCon.2016.7831042, 2016.
K. K. Mehta and R. J. Ram, "Precise and diffraction-limited waveguide-to-free-space focusing gratings," arXiv 1607.00107, 2016.
David Fattal, Zhen Peng, Tho Tran, Sonny Vo, Marco Fiorentino, Jim Brug & Raymond G. Beausoleil, "A multi-directional backlight for a wide-angle, glasses-free three-dimensional display", Nature 495, 348, 2013.
Martijn J. R. Heck, "Highly integrated optical phased arrays: photonic integrated circuits for optical beam shaping and beam steering". Nanophotonics, 6(1): 93-107, doi: 10.1515/nanoph-2015-0152, 2017.
Trevor K. Chan, Mischa Megens, Byung-Wook Yoo, John Wyras, Connie J. Chang-Hasnain, Ming C. Wu, and David A. Horsley, "Optical beamsteering using an 8×8 MEMS phased array with closed-loop interferometric phase control", Opt Express; 21:2807-15, 2013.
M. Raval, C. Poulton, and M. R. Watts, "Unidirection waveguide grating antennas with uniform emission for optical phased arrays", Optics Letters, v. 42, No. 12, doi: 10.1364/OL.42.002563, 2017.
A. Femius Koenderink, Andrea Alù, Albert Polman, "Nanophotonics: Shrinking light-based technology", Science, v. 348, No. 6234, doi: 10.1126/science.1261243, 2015.
Mikhail I. Shalaev, Jingbo Sun, Alexander Tsukernik, Apra Pandey, Kirill Nikolskiy, and Natalia M. Litchinitser, "High-Efficiency All-Dielectric Metasurfaces for Ultracompact Beam Manipulation in Transmission Mode", Nano Letters, 15 (9), pp. 6261-6266, doi: 10.1021/acs.nanolett.5b02926, 2015.
Paul J. M. Suni, John Bowers, Larry Coldren, S.J. Ben Yoo, "Photonic Integrated Circuits for Coherent Lidar", 18th Coherent Laser Radar Conference, CLRC 2016, Jun. 26-Jul. 1, 2016.
Chao Li, Huijuan Zhang, Mingbin Yu, and G. Q. Lo, "CMOS-compatible High Efficiency Double-Etched Apodized Waveguide Grating Coupler", Opt. Expr., 21, pp. 7868, 2013.
Christopher Vincent Poulton, "Integrated LIDAR with Optical Phased Arrays in Silicon Photonics", MIT MS EECS Thesis, Sep. 2016.
S. J. Ben Yoo, Binbin Guan and Ryan P. Scott, "Heterogeneous 2D/3D Photonic Integrated Microsystems", Microsystems & Nanoengineering, v. 2, 16030; doi:10.1038/micronano.2016.30, 2016.
Francesco Aieta, Patrice Genevet, Nanfang Yu, Mikhail A. Kats, Zeno Gaburro, and Federico Capasso. "Out-of-Plane Reflection and Refraction of Light by Anisotropic Optical Antenna Metasurfaces with Phase Discontinuities", Nano Lett., 12 (3), pp. 1702-1706, doi: 10.1021/nl300204s, 2012.
Paul F. McManamon, Philip J. Bos, Michael J. Escuti, Jason Heikenfeld, Steve Serati, HuikaiXie, Edward A. Watson , "A Review of Phased Array Steering for Narrow-Band Electrooptical Systems", Proc. of the IEEE, 97, pp. 1078, doi: 10.1109/JPROC.2009.2017218, 2009.
Byung-Wook Yoo, Mischa Megens, Tianbo Sun, Weijian Yang, Connie J. Chang-Hasnain, David A. Horsley, and Ming C. Wu, "A 32×32 Optical Phased Array Using Polysilicon Sub-Wavelength High-Contrast-Grating Mirrors", Opt. Expr., 22, doi:10.1364/OE.22.019029, 2014.
Weihua Guo, Pietro R. A. Binetti, Chad Althouse , Milan L. Mašanović, Huub P. M. M. Ambrosius, Leif A. Johansson, Larry A. Coldren, "Two-Dimensional Optical Beam Steering with InP-based Photonic Integrated Circuits," IEEE J. Sel. Topics Quantum Electron., Special Issue on Semiconductor Lasers, 19, pp. 6100212, 2013.
J. C. Hulme, J. K. Doylend, M. J. R. Heck, J. D. Peters, M. L. Davenport, J. T. Bovington, L. A. Coldren, and J. E. Bowers, "Fully Integrated Hybrid Silicon Two Dimensional Beam Scanner", Optics Express, vol. 23, No. 5 doi:10.1364/OE.23.005861, p. 5861-5874; Feb. 25, 2015.
Brian W. Krause, Bruce G. Tiemann, and Philip Gatt, "Motion Compensated Frequency Modulated Continuous Wave 3D Coherent Imaging Ladar with Scannerless Architecture," Appl. Opt., 51, pp. 8745-8761 (2012).
Fei Ding, Zhuoxian Wang, Sailing He, Vladimir M. Shalaev, and Alexander V. Kildishev, "Broadband High-Efficiency Half-Wave Plate: A Supercell-Based Plasmonic Metasurface Approach", ACS Nano, doi: 10.1021/acsnano.5b00218, 2015.
Hooman Abediasl and Hossein Hashemi, "Monolithic optical phased-array transceiver in a standard SOI CMOS process", Opt. Express 23, 6509, doi: 10.1364/OE.23.006509, 2015.
David N. Hutchison, Jie Sun, Jonathan K. Doylend, Ranjeet Kumar, John Heck, Woosung Kim, Christopher T. Phare, Avi Feshali, and Haisheng Rong, "High-resolution aliasing-free optical beam steering", Optica 3, 887, doi: 10.1364/OPTICA.3.000887, 2016.
Firooz Aflatouni, Behrooz Abiri, Angad Rekhi, and Ali Hajimiri, "Nanophotonic coherent imager", Opt. Express 23, doi: 10.1364/OE.23.005117, 2015.
Tin Komljenovic, Roger Helkey, Larry Coldren, and John E. Bowers, "Sparse aperiodic arrays for optical beam forming and LIDAR", Opt. Express 25, 2511, doi: 10.1364/OE.25.002511, 2017.
Binbin Guan, Ryan P. Scott, Chuan Qin, Nicolas K. Fontaine, Tiehui Su, Carlo Ferrari, Mark Cappuzzo, Fred Klemens, Bob Keller, Mark Earnshaw, and S. J. B. Yoo, "Free-space coherent optical communication with orbital angular momentum multiplexing/demultiplexing using a hybrid 3D photonic integrated circuit", Opt. Express 22, 145, doi: 10.1364/OE.22.000145, 2014.
William S. Rabinovich ; Peter G. Goetz ; Marcel Pruessner ; Rita Mahon ;Mike S. Ferraro ; Doe Park ; Erin Fleet ; Michael J. DePrenger, "Free space optical communication link using a silicon photonic optical phased array", Proc. SPIE 9354, 93540B, doi:10.1117/12.2077222, 2015.
J. Sun, "Toward accurate and large-scale silicon photonics," MIT Ph.D. Thesis, 2013.
Drexler et al., Optical Coherence Tomography: Technology and Applications. 2nd ed. Springer International Publishing, Switzerland. 2015. Cover page and table of contents only, 9 pages.
Kerstin Worhoff, Rene M. De Ridder, B. Imran Akca, Markus Pollnau, "Silicon Oxynitride Technology for Integrated Optical

(56) References Cited

OTHER PUBLICATIONS

Solutions in Biomedical Applications", In: 13th International Conference on Transparent Optical Networks 2011, Jun. 26-30, 2011, Stockholm, Sweden.
Dietrich, et al., In situ 3D Nanoprinting of Free-form Coupling Elements for Hybrid Photonic Integration, Nature Photonics, Apr. 2018, pp. 241-247, vol. 12, Macmillan Publishers Limited.
Muhammad Rodlin Billah, et al., Hybrid Integration of Silicon Photonics Circuits and InP Lasers by Photonic Wire Bonding, Jul. 2018, vol. 5, No. 7, pp. 876-883, Optica.
Dietrich, et al., In situ 3D Nanoprinting of Free-form Coupling Elements for Hybrid Photonic Integration, Nature Photonics, Apr. 2018, pp. 1-5, vol. 12, Macmillan Publishers Limited.
Trappen, et al. 3D-Printed Optics for Wafer-Scale Probing, 3 pages.
Kaicheng Liang, et al., "Cycloid Scanning for Wide Field Optical Coherence Tomography Endomicroscopy and Angiography in Vivo", Optica, Jan. 2018, pp. 36-43, vol. 5, No. 1.
U.S. Appl. No. 16/864,056, filed Apr. 30, 2020, USPTO.
Hitzenberger, Christoph K., et at., In Vivo Intraocular Ranging by Wavelength Tuning Interferometry, SPIE, pp. 47-51, vol. 3251, retrieved from: http://proceedings.spiedigitallibrary.org/ on Sep. 24, 2013.
Warren L. Stutzman and Gary A. Thiele, "Antena Theory and Design", John Wiley & Sons, ISBN 0-471-04458-X, 1981. Textbook.
Y. Zhao, Z. Chen, C. Saxer, S. Xiang, J.F. de Beor, and J.S. Nelson, "Phase-resolved optical coherence tomography and optical Doppler tomography for imaging blood flow in human skin with fast scanning speed and high velocity sensitivity," Opt. Lett. 25(2), 114-116 (2000).
W. Choi, B. Potsaid, V. Jayaraman, B. Baumann, I. Grulkowski, J. J. Liu, C. D. Lu, A. E. Cable, D. Huang, J. S. Duker, and J. G. Fujimoto, "Phase sensitive swept-source optical coherence tomography imaging of the human retina with a vertical cavity surface-emiting laser light source," Opt. Lett. 38(3), 338-340 (2013).
Youxin Mao, Costel Flueraru, Shoude Chang, Dan P. Popescu, Michael G. Sowa, "Preormance analysis of a swept-source optical coherence tomography system with a quadrature interferometer and optical amplification", Optics Communications, vol. 284, Issues 10-11, May 15, 2011.
C.M. Eigenwillig, B. R. Biedermann, G. Palte, and R. Huber, "K-space linear Fourier domain mode locked laser and applications for optical coherence tomography," Optics Express 16(12), 8916-8937 (2008).
Yizheng Zhu, Neil G. Terry, and Adam Wax, "Scanning fiber angle-resolved low coherence interferometry", Optics Letters, vol. 34, No. 20, 2009.
Michael Giacomelli, Yizheng, Zhu, John Lee, Adam Wax, "Size and shape determination of spheroidal scatters using two-dimensional angle resolved scattering",Optics Express, vol. 18, No. 14, 2010.
Humle, J.C. et al., "Fully integrated hybrid silicon free-space beam steering source with 32 channel phased array" International Society for Optics and Photonics (SPIE PW), San Francisco, CA Feb. 1-6, 2014, pp. 898907-1-898907-15.
Kevin Gourley, Ilya Golu, Brahim Chebbi, "First experimental demonstration of a Fresnel Axicon", Proceedings of the SPIE, doi:10.1117/12.807162, Jun. 18, 2008.
Oto Brzobohatý, TomášČižmár, and Pavel Zemánek, "High quality quasi-Bessel beam generated by round-tip axicon", Optics Express, vol. 16, No. 17, 2008.
S. Yerolatsitis, I. Gris-Sánchez, T. A. Birks, "Tapered Mode Multiplexers for Single Mode to Multi Mode Fibre Mode Transitions", Proceedings of the Optical Fiber Communications Conference, Paper w3B.4, 2015.
A. M. Velazquez-Benitez, J. C. Alvarado, G. Lopez-Galmiche, J. E. Antonio-Lopez, J. Hernández-Cordero, J. Sanchez-Mondragon, P. Sillard, C. M. Okonkwo, and R. Amezcua-Correa, "Six mode selective fiber optic spatial multiplexer", Optics Letters, vol. 40, No. 8, Apr. 15, 2015.

Semard Oduro, Rand Ismaeel, Timothy Lee and Gilberto Brambilla, "Selective Excitation of High Order Modes in Few Mode Fibres Using Optical Microfibres", Proceedings of the Optical Fiber Communications Conference, Paper M3D.5, 2015.
S. U. Alam*, Y. Jung, Q. Kang, F. Poletti, J.K. Sahu and D. J. Richardson, "Recent Progress in the Development of Few Mode Fiber Amplifiers", Proceedings of the Optical Fiber Communications Conference, Paper Tu3C.1, 2015.
R. Ryf, N. K. Fontaine1, M. Montoliu, S. Randell, B. Ercan, H. Chen, S. Chandrasekhar, A. H. Gnauck, S. G. Leon-Saval, J. Bland-Hawthom, J. R. Salazar-Gil, Y. Sun, R. Lingle, Jr., "Photonic-Lantern-Based Mode Multiplexers for Few-Mode-Fiber Transmission", Proceedings of the Optical Fiber Communications Conference, Paper W4J.2., 2015.
Sergio G. Leon-Saval, Nicolas K. Fontaine, Joel R. Salazar-Gil, Burcu Ercan, Roland Ryf, and Joss Bland-Hawthorn, "Mode-selective photonic lanterns for space division multiplexing", Optics Express, vol. 22, No. Jan. 13, 2014.
Haoshuo Chen, Nicolas K. Fontaine, Roland Ryf, Binbin Guan, S. J. Ben Yoo, and Ton (A. M. J.) Koonen, "Design Constraints of Photonic-Lantern Spatial Multiplexer Based on Laser-Inscribed 3-D Waveguide Technology", Journal of Lightwave Technology, vol. 33, No. 6, Mar. 15, 2015.
Haoshuo Chen, Roy van Uden, Chigo Okonkwo, and Ton Koonen, "Compact spatial multiplexers for mode division multiplexing", Optics Express, vol. 22, No. 26, Dec. 26, 2014.
Simon Schneider, Matthias Lauermann, Philipp-Immanuel Dietrich, Claudius Weimann, Wolfgang Freude, and Christian Koos, Optical coherence tomography system mass producible on a silicon photonic chip, Optics Express, vol. 24, No. 2, Jan. 2016.
Eduardo Margallo-Balb'as, Gregory Pandraud and Patrick J. French, "Miniature Optical Coherence Tomography System Based on Silicon Photonics", SPIE 2Proceedings, vol. 6847 (2008).
Christopher R. Doerr and Lawrence L. Buhl, "Circular Grating Coupler for Creating Focused Azimuthally and Radially Polarized Beams", Optics Letters, vol. 36, No. 7, Apr. 1, 2011.
Nenad Bozinovic, Yang Yue, Yongxiong Ren, Moshe Tur, Poul Kristensen, Hao Huang, Alan E. Willner, Siddharth Ramachandran, "Terabit-Scale Orbital Angular Momentum Mode Division Multiplexing in Fibers", Science Magazine, vol. 340 Jun. 28, 2013.
D. Huang. E. A. Swanson, C. P. Lin, J. S. Schuman, W. G. Stinson, W. Chang, M. R. Hee, t. Flotte, K. Gregory, C. A. Puliafito and J. G. Fujimoto, "Optical coherence tomography," Science 254(5035), 1178-1181 (1991).
R. Leitgeb, C. Hitzenberger, and A. Fercher, "Performance of fourier domain vs. time domain optical coherence tomography," OPt. Express 11(8), 889-894 (2003).
J. F. de Boer, B. Cense, B. H, Park, M. C. Pierce, G. J. Tearney, and B. E. Bouma, "Improved signal-to-noise ratio in spectral-domain compared with time-domain optical coherence tomography," Opt. Lett. 28(21), 2067-2069 (2003).
M. Choma, M. Sarunic, C. Yang, and J. Izatt, "Sensitvity advantage of swept source and fourier domain optical coherence tomography," Opt. Express 11(18), 2183-2189 (2003).
M. Wojtkowski, A, Kowalczyk, R. Leitgeb, and A. F. Fercher, "Full range complex spectral optical coherence tomography technique in eye imaging," Opt. lett. 27(16), 1415-1417 (2002).
A. F. Fercher, C. K. Hitzenberger, G. Kamp, and S. Y. El-Zaiat, "Measurement of intraocular distances by backsattering spectral interferometry," Opt. Commun. 117(1), 43-48 (1995).
S. R. Chinn, E. A. Swanson, and J. G. Fujimoto, "Optical cohoerence tomography using a frequency-tunable optical source," Opt. Lett. 22(5), 340-342 (1997).
S. Yun, G. Tearney, J. de Boer, N. Iftima, and B. Bouma, "High-speed optical frequency-domain imaging," Opt. Express 11(22), 2953-2963 (2003).
R. Huber, M. Wojtkowski, and J.G. Fujimoto, "Fourier Domain Mode Locking (FDML): A new laser operating regime and applications for optical coherence tomography," Opt Express 14(8), 3225-3237 (2006).

(56) References Cited

OTHER PUBLICATIONS

R. Huber, D. C. Adler, and J. G, Fujimoto, "Buffered Fourier domain mode locking: unidirectional swept laser sources for optical coherence tomography imaging at 370,000 lines/s," Opt. Lett.31(20), 2975-2977 (2006).

B. Potsaid, V. Jayaraman, J. G. Fujimoto, J. Jiang, P. J. Heim, and A. E. Cable, "MEMS tunable VCSEL light source for ultrahigh speed 60kHz-1MHz axial scan rate and long range centimeter class OCT imaging," in SPIE BiOS, (International Society for Optics and Photonics), (2012).

V. Jayaraman, G. D. Cole, M. Robertson, A. Uddin, and A. Cable, "High-sweep-rate 1310 nm MEMS-VCSEL with 150 nm continuous tuning range," Electron. Lett. 48(14), 867-869 (2012).

W. Wieser, W. Draxinger, T. Klein, S. Karpf, T. Pfeiffer, and R. Huber, "High definition live 3D-OCT in vivo: design and evaluation of a 4D OCT engine with 1 GVoxel/s," Biomed. Opt. Express 5(9), 2963-2977 (2014).

M.V. Sarunic, B.E. Applegate, and J.Izatt, "Real-Time Quadrature Projection Complex Conjugate Resolved Fourier Domain Optical Coherence Tomography," Optics Letters, vol. 31, No. 16, Aug. 15, 2006.

R. K. Wang, S. L. Jacques, Z. Ma, S. Hurst, S. R. Hanson, and A. Gruber, "Three dimensional optical angiography," Opt Express 15(7), 4083-4097 (2007).

Y. Jia, O. Tan, J. Tokayer, B. Potsaid, Y. Wang, J. J. Liu, M. F. Kraus, H. Subhash, J. G. Fujimoto, J. Hornegger, and D. Huang, "Split-spectrum amplitude-decorrelation angiography with optical coherence tomography," Opt. Express 20(4), 4710-4725 (2012).

S. Makita, Y. Hong, M. Yamanari, T. Yatagai, and Y. Yasuno, "Optical coherence angiography," Opt. Express 14(17), 7821-7840 (2006).

S. Yazdanfar, M. Kulkarni, and J. Izatt, "High resolution imaging of in vivo cardiac dynamics using color Doppler optical coherence tomography," Opt. Express 1(13), 424-431 (1997).

B. Vakoc, S. Yun, J. de Boer, G. Tearney, and B. Bouma, "Phase-resolved optical frequency domain imaging," Opt. Express 13(14), 5483-5493 (2005).

M. R. Hee, E. A. Swanson, J. G. Fujimoto, and D. Huang, "Polarization-sensitive low-coherence reflectometer for birefringence characterization and ranging," J. Opt. Soc. Am. B 9(6), 903-908 (1992).

J. F. de Boer and T. E. Milner, "Review of polarization sensitive optical coherence tomography and Stokes vector determination," J. Biomed. Opt. 7(3), 359-371 (2002).

M. Pircher, C. K. Hitzenberger, and U. Schmidt-Erfurth, "Polarization sensitive optical coherence tomography in the human eye," Prog. Retin. Eye. Res. 30(6), 431-451 (2011).

S. K. Nadkarni, M. C. Pierce, B. H. Park, J. F. de Boer, P. Whittaker, B. E. Bouma, J. E. Bressner, E. Halpern, S. L. Houser, and G. J. Tearney, "Measurement of Collagen and Smooth Muscle Cell Content in Atherosclerotic Plaques Using Polarization-Sensitive Optical Coherence Tomography," J. Am. Coll. Cardiol. 49(13), 1474-1481 (2007).

B. R. Biedermann, W. Wieser, C. M. Eigenwillig, T. Klein, and R. Huber, "Dispersion, coherence and noise of Fourier domain mode locked lasers," Opt. Express 17(12), 9947-9961 (2009).

M. Sarunic, M. A. Choma, C. Yang, and J. A. Izatt, "Instantaneous complex conjugate resolved spectral domain and swept-source OCT using 3×3 fiber couplers," Opt. Express 13(3), 957-967 (2005).

R. K. Wang, "In vivo full range complex Fourier domain optical coherence tomography," Appl. Phys. Lett. 90(5), 054103 (2007).

M. Yamanari, S. Makita, Y. Lim, and Y. Yasuno, "Full-range polarization-sensitive swept-source optical coherence tomography by simultaneous transversal and spectral modulation," Opt. Express 18(13), 13964-13980 (2010).

K. Takiguchi, et al., "Integrated-optic variable delay line and its application to a low-coherence reflectometer", Optics Letters, Oct. 15, 2005, pp. 2739-2741, vol. 30, No. 20, Optical Society of America.

Mahmoud S. Rasras, et al., "Integrated resonance-enhanced variable optical delay lines", IEEE Photonics Technology Letters, Apr. 4, 2005, pp. 834-836, vol. 17, No. 4.

Leimeng Zhuang, et al., "Low-loss, high-index-contrast Si3N4/SiO2 optical waveguides for optical delay lines in microwave photonics signal processing", Optics Express, Oct. 17, 2011, pp. 23162-23170, vol. 19, No. 23.

J.P. Mack, et al., "Photonic Integrated Circuit Switch Matrix and Waveguide Delay Lines for Optical Packet Synchronization" ECOC 2008, Sep. 21-25, 2008, pp. 87-88, vol. 4, IEEE, Brussels, Belgium.

Jingya XIE, et al., "Seven-bit reconfigurable optical true time delay line based on silicon integration", Optics Express, Sep. 22, 2014, pp. 22707-22715 vol. 22, No. 19.

Hansuek Lee et al., "Ultra-low-loss optical delay line on a silicon chip", Nature Communications, May 2012, 7 pages.

Xiaolong Wang, et al., "Phase error corrected 4-bit true time delay module using a cascaded 2×2 polymer waveguide switch array" Applied Optics, Jan. 20, 2007, pp. 379-383 vol. 46, No. 3.

Maciej Wojtkowski, et al., "Ultrahigh-resolution, high-speed, Fourier domain optical coherence tomography and methods for dispersion compensation", Optics Express, May 31, 2004, pp. 2404-2422, vol. 12, No. 11.

Dierck Hillmann et al., "Common approach for compensation of axial motion artifacts in swept-source OCT and dispersion in Fourier-domain OCT", Optics Express, Mar. 12, 2012, pp. 6761-6676, vol. 20, No. 6.

Norman Lippok, et al., "Dispersion compensation in Fourier domain optical coherence tomography using the fractional Fourier transform", Optics Express, Oct. 8, 2012, pp. 23398-23413, vol. 20, No. 1.

Kaname Jinguji, et al., "Two-port optical wavelength circuits composed of cascaded Mach-Zehnder interferometers with point-symmetrical configurations", Journal of Lightwave Technology, Oct. 10, 1996, pp. 2301-2310, vol. 14, No. 10.

Xingchen JI, et al., "On-chip tunable photonic delay line", APL Photonics, 2019, pp. 090803-1-090803-7, 4doi 10.1063/1.5111164.

EunSeo Choi, et al., "All-fiber variable optical delay line for applications in optical coherence tomography: feasibility study for a novel delay line", Optics Express, Feb. 21, 2005, pp. 1334-1345, vol. 13, No. 4.

Hailong Zhou, et al., "All-in-one silicon photonic polarization processor", Nanophotonics, 2019, pp. 2257-2267, vol. 8, No. 12.

Fred Heismann, "Analysis of a Reset-Free Polarization Controller for Fast Automatic PolarizationStabilization in Fiber-optic Transmission Systems", Journal of Lightwave Technology, Apr. 1994, pp. 690-699, vol. 12, No. 4.

Reinhold Noe, et al., "Automatic endless polarization control with integrated-optical Ti:LiNbO3 polarization transformers", Reinhold Noe, Optics Letters, Jun. 1988, pp. 527-529, vol. 13, No. 6.

Tao Chu, et al., "Compact 1 Å~N thermo-optic switches based on silicon photonic wire waveguides", Optics Express, Dec. 12, 2005, pp. 10109-10114, vol. 13, No. 25.

Xiaoxi Wang, et al., "Compact high-extinction-ratio silicon photonic variable optical attenuators (VOAs)," Proceedings of the Conference on Lasers and Electro Optics (CLEO), 2 pages, Paper SW1N.7, 2017.

Reinhold Noe, et al., "Endless Polarization Control Systems for Coherent Optics", Journal of Lightwave Technology, Jul. 1988, pp. 1199-1208, vol. 6, No. 7.

Ansheng Liu, et al., "High-speed optical modulation based on carrier depletion in a silicon waveguide", Optics Express Jan. 22, 2007, pp. 660-668, vol. 15, No. 2.

Niels Quack, et al., "MEMS-Enabled Silicon Photonic Integrated Devices and Circuits", IEEE Journal of Quantum Electronics, Feb. 2020, vol. 56, No. 1.

Christopher R. Doerr, et al., "Monolithic PDM-DQPSK receiver in silicon", 36th European Conference and Exhibition on Optical Communication 2010 3 pages.

Benjamin G. Lee, et al., "Silicon Photonic Switch Fabrics: Technology and Architecture", Journal of Lightwave Technology, DOI 10.1109/JLT.2018.2876828, 2018, 15 pages.

(56) References Cited

OTHER PUBLICATIONS

Xin Tu, et al., "State of the Art and Perspectives on Silicon Photonic Switches", Micromachines, 2019, 19 pages, vol. 10, No. 55, doi:10.3390/mi10010051.

Richard Soref, "Tutorial: Integrated-photonic switching structures", APL Photonics, Jan. 29, 2018, 19 pages, doi.org/10.1063/1.5017968.

Benjamin Koch, et al., "Versatile endless optical polarization controller/tracker/demultiplexer", Optics Express, Apr. 7, 2014, pp. 8259-8276, vol. 22, No. 7.

P. Velha, et al., "Wide-band polarization controller for Si photonic integrated circuits", Optics Letters, Dec. 15, 2016, pp. 5656-5659, vol. 41, No. 21.

B. Imran Akca, "Non-moving scanner design for OCT systems", Optics Express, Dec. 12, 2016, vol. 24, No. 25.

Meena Siddiqui, et al., "High-speed optical coherence tomography by circular interferometric ranging", Nature Photonics, Nature Photonics, Feb. 2018, vol. 12.

Luis A. Bru, et al., "Integrated optical frequency domain reflectometry device for characterization of complex integrated devices", Optics Express, Nov. 12, 2018, vol. 26, No. 23, doi:10.1364/OE.26.030000.

U.S. Appl. No. 15/147,775, filed Dec. 8, 2016, USPTO.

G. Roelkens, D. Vermeulen, S. Selvaraja, Student Member, IEEE, R. Halir, W. Bogaerts, Member, IEEE, and D. Van Thourhout, "Grating-Based Optical Fiber Interfaces for Silicon-on-Insulator Photonic Integrated Circuits", IEEE Journal of Selected Topics in Quantum Electronics, vol. 17, No. 3, May/Jun. 2011.

Attila Mekis, Steffen Gloeckner, Gianlorenzo Masini, Adithyaram Narasimha, Member, IEEE, Thierry Pinguet, Subal Sahni, and Peter De Dobbelaere,"A Grating-Coupler-Enabled CMOS Photonics Platform". IEEE Journal of Selected Topics in Quantum Electronics, vol. 17, Issue 3, May/Jun. 2011.

Neil Na, Harel Frish, I-Wei Hsieh, Oshrit Harel, Roshan George, Assia Barkai, and Haisheng Rong, "Efficient broadband silicon-on-insulator grating coupler with low backreflection", Optics Letters, vol. 36, No. 11, Jun. 1, 2011.

Wissem Sfar Zaoui, Marfa Félix Rosa, Wolfgang Vogel, Manfred Berroth Jörg Butschke, and Florian Letzkus, "Cost-effective CMOS-compatible grating couplers with backside metal mirror and 69% coupling efficiency", Optics Express, vol. 20, No. 26, Dec. 10, 2012.

Vilson R. Almeida, Roberto R. Panepucci, and Michal Lipson, "Nanotaper for compact mode conversion", Optics Letters, vol. 28, No. 15, Aug. 1, 2003.

Anatol Khilo, Miloš A. Popovic, Mohammad Araghchini, and Franz X. Kärtner, "Efficient planar fiber-to-chip coupler based on two-stage adiabatic evolution", Optics Express, vol. 18, No. 15, Jul. 19, 2010.

Long Chen, Christopher R. Doerr, Young-Kai Chen, and Tsung-Yang Liow, "Low-Loss and Broadband Cantilever Couplers Between Standard Cleaved Fibers and High-Index-Contrast Si3N4 or Si Waveguides", IEEE Photonics Technology Letters, vol. 22, No. 23, Dec. 1, 2010.

Alan Y. Liu, Chong Zhang, Justin Norman, Andrew Snyder, Dmitri Lubyshev,Joel M. Fastenau, Amy W. K. Liu, Arthur C. Gossard, and John E. Bowers, "High performance continuous wave 1.3 Im quantum dot lasers on silicon", Applied Physics Letters, 104, 041104 (2014).

Jie Sun, Erman Timurdogan, Ami Yaacobi, Zhan Su, Ehsan Shah Hosseini, David B. Cole, and Michael R. Watts, "Large-Scale Silicon Photonic Circuits for Optical Phased Arrays", IEEE Journal of Selected Topics in Quantum Electronics, vol. 20, No. 4, Jul./Aug. 2014.

Jie Sun, Ehsan Shah Hosseini, Ami Yaacobi, David B. Cole, Gerald Leake, Douglas Coolbaugh, and Micheael R. Watts, "Two-dimensional apodized silicon photonic phased arrays", Optics Letters, vol. 39, No. 2, Jan. 15, 2014.

C. T. DeRose, R. D. Kekatpure, D. C. Trotter, A. Starbuck. J. R. Wendt, A. Yaacobi, M. R. Watts, U. Chettiar, N. Engheta, and P. S. Davids, "Electronically controlled optical beam-steering by an active phased array of metallic nanoantennas", Optics Express, vol. 21, No. 4, Feb. 25, 2013.

Jie Sun, Erman Timurdogan, Ami Yaacobi, Ehsan Shah Hosseini, and Michel R. Watts, "Large-scale nanophotonic phased array", Nature, vol. 493, Jan. 10, 2013.

Ami Yaacobi Erman Timurdogan, and Michael R. Watts, "Vertical emitting aperture nanoantennas", Optics Letters, vol. 37, No. 9, May 1, 2012.

J. K. Doylend, M. J. R. Heck, J. T. Bovington, J. D. Peters, L. A. Coldre, and J. E. Bowers, "Two-dimensional free-space beam steering with an optical phased array of silicon-on-insulator", Optics Express, vol. 19, No. 22, Oct. 24, 2011.

Karel Van Acoleyen, Hendrick Rogier, and Roel Baets, "Two-dimensional optical phased array antenna on silicon-on-insulator", Optics Express, vol. 18, No. 13, Jun. 21, 2010.

James A. Burns, Brian F. Aull, Chenson K. Chen, Chang-Lee Chen, Craig L. Keast, Jeffrey M. Knecht, Vyshanavi Suntharalingam, Keith Warner, Peter W. Wyatt, and Donna-Ruth W. Yost, "A Wafer-Scale 3-D Circuit Integration Technology", IEEE Transactions on Electronic Devices, vol. 53, No. 10, Oct. 2006.

Dirk Lorenser, C. Christian Singe, Andrea Curatolo, and David D. Sampson, "Energy-efficient low-Fresnel-number Bessel beams and their application in optical coherence tomography", Optics Letters, vol. 39, No. 3, Feb. 1, 2014.

Niklas Weber, Dominik Spether, Andreas Seifert, and Hans Zappe, "Highly compact imaging using Bessel beams generated by ultraminiaturized multi-micro-axicon systems", Journal of Optical Society of America A. vol. 29, No. 5, May 2012.

Z. Xie, B. Armbruster, and T. Grosjean, "Axicon on a gradient index lens (AXIGRIN)): integrated otial bench for Bessel beam generation from a point-like source", Applied Optics, vol. 53, Issue 26, (2014).

G.S. Sokolovskii, V.V. Dudelev, S.N. Losev, K.K. Soboleva, A.G. Deryagin, K.A. Fedorovac, V.I. Kuchinskii, W. Sibbett, E.U. Rafailov, "Bessel beams from semiconductor light sources", Progress in Quantum Electronics, vol. 38, No. 4, Jul. 2014.

F. Merola ; S. Coppola ; V. Vespini ; S. Grilli ; P. Ferraro ; D. Balduzzi ; A. Galli ; R. Puglisi,"Fabrication and test of polymeric microaxicons", Apr. 16-19, 2012, Proceedings of the SPIE, doi:10.1117/12.922572.

Paul Steinvurzel, Khwanchai Tantiwanichapan, Masao Goto, and Siddharth Ramachandran, "Fiber-based Bessel beams with controllable diffraction-resistant distance", Optics Letters, vol. 36, No. 23, 2011.

Cedric Blatter; Branislav Grajciar ; Christoph M. Eigenwillig; Wolfgang Wieser; Benjamin R. Biedermann; Robert Huber; Rainer A. Leitgeb, "High-speed functional OCT with self-reconstructive Bessel illumination at 1300 nm", Proceedings of the SPIE, doi:10.1117/12.889669, Jun. 1, 2011.

James G. Fujimoto, Eric Swanson, Robert Huber, European Inventor Award 2017, Jun. 15, 2017, 3 pages. PRWeb.

Manon Rostykus, and Christophe Moser, "Compact lensless off-axis transmission digital holographic microscope," Opt Ex. 25(14), 16652-16659 (2017).

Damien Loterie, Demetri Psaltis, and Christophe Moser, "Bend translation in multimode fiber imaging," Opt. Ex. 25(6), 6263-6273 (2017).

Edgar E. Morales-Delgado, Demetri Psaltis, and Christophe Moser, "Two-photon imaging through a multimode fiber," Opt. Ex. 23(25), 32158-32170 (2015).

Damien Loterie, Sebstianus A. Goorden, Demetrie Psaltis, and Christophe Moser, "Confocal microscopy through a multimode fiber using optical correlation," Opt. Lett. 40(24), 5754-5757 (2015).

Siddharth Sivankutty, Esben Ravn Andresen, Rosa Cossart, Geraud Bouwmans, Serge Monneret, and Herve Rigneault, Ultra-thin rigid endoscope: two-photon imaging through a graded-index.

Sean C. Warren, Youngchan Kim, James M. Stone, Claire Mitchell, Jonathan C. Knight, Mark A. A. Neil, Carl Paterson, Paul M. W. French, and Chris Dunsby, "Adaptive multiphoton endomicroscopy through a dynamically deformed multicore optical fiber using proximal detection," Opt. Ex. 24(19), 21474-21484 (2016).

(56) References Cited

OTHER PUBLICATIONS

Alexander Fertman and Dvir Yelin, "Image transmission through an optical fiber using real-time modal phase restoration," JOSAB 30(1), 149-157 (2013).

Mickael Mounaix, Hilton B. de Aguiar, and Sylvain Gigan, "Temporal recompression through a scattering medium via a broadband transmission matrix," ArXiv (2017).

S. M. Popoff, G. Lerosey, R. Carminati, M. Fink, A.C. Boccara, and S. Gigan, "Measuring the Transmission Matrix in Optics : An Approach to the Study and Control of Light Propagation in Disordered Media," Phys. Rev. Lett. 104(10), 100601-100605 (2010).

Jürgen W. Czarske, Daniel Haufe, Nektarios Koukourakis, and Lars Büttner, "Transmission of independent signals through a multimode fiber using digital optical phase conjugation," Opt. Ex. 24(13), 15128-15136 (2016).

J. M. Stone, H. A. C. Wood, K. Harrinton, and T. A. Birks, "Low index contrast imaging fibers," Opt. Lett. 42(8), 1484-1487 (2017).

Harry A. C. Wood, Kerrianne Harrington, James M. Stone, Tim A. Birks, and Jonathan C. Knight, "Quantitative characterization of endoscopic imaging fibers," Opt. Ex 25(3), 1985-1992 (2017).

Antonio M. Caravaca-Aguirre and Rafael Piestun, "Single multimode fiber endoscope," Opt Ex. 25(3), 1656-1665 (2017).

Ivan Gusachenko, Mingahou Chen, and Kishan Dholakia, "Raman imaging through a single multimode fibre," Opt. Ex. 25(12), 13782-13798 (2017).

Tomas Cizmar, and Kishan Dholakia, "Shaping the light transmission through a multimode optical fibre: complex transformation analysis and applications in biophotonics," Opt. Ex. 19(20), 18871-8884 (2011).

Moussa N'Gom, Theodore B. Norris, Eric Michielssen, Raj Rao Nadakuditi, "Mode Control in a Multimode Fiber Through Acquiring its Transmission Matrix from a Reference-less Optical System," ArXiv (2017).

Roberto Di Leonardo and Silvio Bianchi, "Hologram transmission through multi-mode optical fibers," Opt. Ex. 19(1), 247-254 (2011).

Carmelo Rosales-Guzman, Nkosiphile Bhebhe, Nyiku Mahonisi, and Andrew Forbes, "Multiplexing 200 modes on a single digital hologram," ArXiv (2017).

Peng Lu, Matthew Shipton, Anbo Wang, Shay Soker, and Yong Xu, "Adaptive control of waveguide modes in a two-mode fiber," Opt. Ex. 22(3), 2955-2964 (2014).

Shamir Rosen, Doron Gilboa, Ori Katz, Yaron Silberberg, "Focusing and Scanning through Flexible Multimode Fibers without Access to the Distal End", 8 pages.

Pablo Eugui, Antonia Lichtenegger, Marco Augustin, Danielle J. Harper, Martina Muck, Thomas Roetzer, Andreas Wartak, Thomas Konegger, Georg Widhalm, Christoph K. Hitzenberger, Adelheid Woehrer, and Bernhard Baumann, Beyond backscattering: Optical neuroimaging by BRAD, arXiv:1712.00361v1 [physics.optics] Dec. 1, 2017.

Carmelo Rosales-Guzmán and Andrew Forbes, "How to Shape Light with Spatial Light Modulators", SPIE Spotlight, doi: http://dx.doi.org/10.1117/3.2281295, 2017.

Lucas B. Soldano and Erik C. M. Pennings, "Optical Multi-Mode Interference Devices Based on Self-Imaging: Principles and Applications", Journal of Lightwave Technology, vol. 13, No. 4, Apr. 1995.

Victor Arrizón, Ulises Ruiz, Rosibel Carrada, and Luis A. González, "Pixelated phase computer holograms for the accurate encoding of scalar complex fields", J. Opt. Soc. Am. A/vol. 24, No. 11/Nov. 2007.

Jeff Demas, Lars Rishøj, and Siddharth Ramachandran*, Free-space beam shaping for precise control and conversion of modes in optical fiber,vol. 23, No. 22 DOI:10.1364/OE.23.028531, 2015.

S. M. Popoff, G. Lerosey, R. Carminati, M. Fink, A.C. Boccara, S. Gigan , "Measuring the Transmission Matrix in Optics: An Approach to the Study and Control of Light Propagation in Disordered Media", arXiv:0910.5436v2 [physics.optics] Jan. 18, 2010.

S. Yun, G. Tearney, J. de Boer, and B. E. Bouma, "Removing the depth-degeneracy in optical frequency domain imaging with frequency shifting," Opt. Express 12(20), 4822-4828 (2004).

B. J. Vakoc, S. H. Yun, G. J. Tearney, and B. E. Bouma, "Elimination of depth degeneracy in optical frequency-domain imaging through polarization-based optical demodulation," Opt. Lett. 31(3), 362-364 (2006).

M. Siddiqui, S. Tozburun, E. Z. Zhang, and B. J. Vakoc, "Compensation of spectral and RF errors in swept-source OCT for high extinction complex demodulation," Opt. Express 23, 5508-5520 (2015).

K.-S. Lee, P. Meemon, W. Dallas, K. Hsu, and J. P. Rolland, "Dual detection full range frequency domain optical coherence tomography," Opt. Lett. 35(7), 1058-1060 (2010).

B. Hofer, B. Považay, B. Hermann, A. Unterhuber, G. Matz, and W. Drexler, "Dispersion encoded full range frequency domain optical coherence tomography," Opt. Express 17(1), 7-24 (2009).

T.-H. Tsai, B. Potsaid, Y. K. Tao, V. Jayaraman, J. Jiang, P. J. S. Heim, M. F. Kraus, C. Zhou, J. Homegger, H. Mashimo, A. E. Cable, and J. G. Fujimoto, "Ultrahigh speed endoscopic optical coherence tomography using micromotor imaging catheter and VCSEL technology," Biomed. Opt. Express 4(7), 1119-1132 (2013).

B. Baumann, W. Choi, B. Potsaid, D. Huang, J. S. Duker, and J. G. Fujimoto, "Swept source Fourier domain polarization sensitive optical coherence tomography with a passive polarization delay unit," Opt. Express 20(9), 10229-10241 (2012).

Z. Wang, H.-C. Lee, O. O. Ahsen, B. Lee, W. Choi, B. Potsaid, J. Liu, V. Jayaraman, A. Cable, M. F. Kraus, K. Liang, J. Hornegger, and J. G. Fujimoto, "Depth-encoded all-fiber swept source polarization sensitive OCT," Biomed. Opt. Express 5(9), 2931-2949 (2014).

B. H. Park, M. C. Pierce, B. Cense, and J. F. de Boer, "Jones matrix analysis for a polarization-sensitive optical coherencetomography system using fiber-optic components," Opt. Lett. 29(21), 2512-2514 (2004).

H. Pahlevaninezhad, A. Lee, L. Cahill, S. Lam, C. MacAulay, and P. Lane, "Fiber-Based Polarization Diversity Detection for Polarization-Sensitive Optical Coherence Tomography," Photonics 1(4), 283-295 (2014).

T. S. Ralston, D. L. Marks, P. S. Carney, and S. A. Boppart, "Interferometric synthetic aperture microscopy," Nat. Phys. 3(2), 129-134 (2007).

U. Morgner, W. Drexler, F. Kärtner, X. Li, C. Pitris, E. Ippen, and J. G. Fujimoto, "Spectroscopic optical coherence tomography," Opt. Lett. 25(2), 111-113 (2000).

R. Huber, M. Wojtkowski, J. G. Fujimoto, J. Y. Jiang, and A. E. Cable, "Three-dimensional and C-mode OCT imaging with a compact, frequency swept laser source at 1300 nm," Optics Express 13(26), 10523-10538 (2005).

R. Huber, M. Wojtkowski, K. Taira, J. G. Fujimoto, and K. Hsu, "Amplified, frequency swept lasers for frequency domain reflectometry and OCT imaging: design and scaling principles," Optics Express 13(9), 3513-3528 (2005).

B. Potsaid, I. Gorczynska, V. J. Srinivasan, Y. L. Chen, J. Jiang, A. Cable, and J. G. Fujimoto, "Ultrahigh speed spectral / Fourier domain OCT ophthalmic imaging at 70,000 to 312,500 axial scans per second," Optics Express 16 (19), 15149-15169 (2008).

Marinko V. Sarunic, Brian E. Applegate, and Joseph A. Izatt, "Real-time quadrature projection complex conjugate resolved Fourier domain optical coherence Tomography", Optics Letters, vol. 31, No. 16, Aug. 15, 2006.

Jiefeng Xi, Li Huo, Jiasong Li and Xingde Li, "Generic real-time uniform K-space sampling method for high-speed swept-Source optical coherence tomography", Optics Express, vol. 18, No. 9, Apr. 26, 2010.

V. Jayaraman, G.D. Cole, M. Robertson, C. Burgner, D. John, A. Uddin and A. Cable, "Rapidly swept, ultra-widely-tunable 1060 nm MEMS-VCSELs", Electronics Letters, Oct. 11, 2012 vol. 48 No. 21.

G. J. Tearney, R. H. Webb, and B. E. Bouma, "Spectrally Encoded Confocal Microscopy", Optics Letters, vol. 23, No. 15, Aug. 1, 1998.

(56) References Cited

OTHER PUBLICATIONS

Chen D. Lu, Martin F. Kraus, Benjamin Potsaid, Jonathan J. Liu, WooJhon Choi, Vijaysekhar Jayaraman, Alex E. Cable, Joachim Hornegger, Jay S. Duker and James G. Fujimoto, "Handheld ultrahigh speed swept source optical coherence tomography instrument using a MEMs scanning mirror", Biomedical Optics Express, vol. 5, No. 1, Jan. 1, 2014.

V. D. Nguyen, N. Weiss, W. Beeker, M. Hoekman, A. Leinse, R. G. Heideman, T. G. van Leeuwen, and J. Kalkman, "Integrated-optics-based swept-source optical coherence tomography," Opt: Lett. 37(23), 4820-4822 (2012).

B. I. Akca, V. Nguyen, J. Kalkman, N. Ismail, G. Sengo, S. Fei, A. Driessen, T. G. van Leeuwen, M. Pollnau, K. Worhoff, and R. M. de Ridder, "Toward Spectral-Domain Optical Coherence Tomography on a Chip," IEEE J. Sel. Top. Quantum Electron. 18(3), 1223-1233 (2012).

V. D. Nguyen, B. I. Akca, K. Wörhoff, R. M. De Ridder, M. Pollnau, T. G. van Leeuwen, and J. Kalkman, "Spectral domain optical coherence tomography imaging with an integrated optics spectrometer," Opt. Lett. 36, 1293-1295 (2011).

G. Yurtsever, B. Považay, A. Alex, B. Zabihian, W. Drexler, and R. Baets, "Photonic integrated Mach-Zehnder Interferometer with an on-chip reference arm for optical coherence tomography," Biomed. Opt. Express 5(4), 1050-1061 (2014).

G. Yurtsever, N. Weiss, J. Kalkman, T. G. van Leeuwen, and R. Baets, "Ultra-compact silicon photonic integrated interferometer for swept-source optical coherence tomography," Opt. Lett. 39(17), 5228-5231 (2014).

B. I. Akca, B. Povazay, A. Alex, K. Worhoff, R. M. de Ridder, W. Drexler, and M. Pallnau, "Miniature spectrometer and beam splitter for an optical coherence tomography on a silicon chip", Optics Express, vol. 31, No. 14, Jul. 3, 2014.

Kyle Preston, Arthur Nitkowski, Nicolas Sherwood-Droz, Andrew Berkeley, Bradley S. Schmid, and Arsen R. Hajian, OCTANE: Optical Coherence Tomography Advanced Nanophotonic Engine, CLEO 2013 Technical Digest, Paper AW31.5, Jun. 9-14, 2013.

Daniel Neill, Luke Stewart, Huiping Li, Tom Killin, Fan Chen, Steve Frisken, Glenn Baxter, Simon Poole, "Compact polarization diverse receiver for biomedical imaging Applications", SPIE Proceedings, vol. 7891, Jan. 22, 2011.

Arthur Nitkowski, Kyle Preston, Nicolás Sherwood-Droz, Andrew Berkeley, Bradford B. Behr, Bradley S. Schmidt, and Arsen R. Hajian, "Nano Spectrometer for Optical Coherence Tomography", Imaging and Applied Optics Conference, Paper AM1B.3, (2013).

B. Imran Akca, "Spectral-Domain Optical Coherence Tomography on a Silicon Chip", PhD Thesis. University of Twente, (2012).

D. Culemann, A. Knuettel, and E. Voges, "Integrated optical sensor in glass for optical coherence tomography," IEEE J. Sel. Topics Quantum Electron., vol. 6, No. 5, pp. 730-734, Oct. 2000.

E. Margallo-Balbas, M. Geljon, G. Pandraud, and P. J. French, "Miniature 10 kHz thermo-optic delay line in silicon," Opt Lett., vol. 35, No. 23, pp. 4027-4029, Dec. 2010.

B. Imran Akca, Markus Pollnau, Kerstin Worhoff, Rene M. De Ridder, "Silicon Oxynitride Technology for Integrated Optical Solutions in Biomedical Applications", In: 13th International Conference on Transparent Optical Networks 2011, Jun. 26-30, 2011, Stockholm, Sweden.

G. Yurtsever, P. Dumon, W. Bogaerts, and R. Baets, "Integrated photonic circuit in silicon on insulator for Fourier domain optical coherence tomography," in Proc. SPIE, Opt. Coherence Tomography Coherence Domain Opt. Methods Biomed. XIV, vol. 7554, San Francisco, CA, 2010, pp. 1-5.

V. D. Nguyen, N. Ismail, F. Sun, K. Worhoff, T. G. van Leeuwen, and J. Kalkman, "SiON integrated optics elliptic couplers for Fizeau-based optical coherence tomography," IEEE J. Lightw. Technol.,Oct. 1, 2010, pp. 2836-2842, vol. 28, No. 19.

Haitham Omran, Yasser M. Sabry, Mohamed Sadek, Khaled Hassan, Mohamed Y. Shalaby and Diaa Khalil, "Deeply-Etched Optical MEMS Tunable Filter for Swept Laser Source Applications", IEEE Photonics Technology Letters. vol. 26, No. 1, Jan. 2014.

Firooz Aflatouni, Behrooz Abiri, Angad Rekhi, and Ali Hajimiri, "Nanophotonic coherent imager", Optics Express, vol. 23, No. 4, doi: 10.1364/OE.23.005117, 2015.

Gyeong Cheol Park, Weiqi Xue, Elizaveta Semenova, Kresten Yvind, Jesper Mørk, and Il-Sug Chung, "III-V/SOI Vertical Cavity Laser with In-plane Output into a Si Waveguide", Paper W2A.17, Proceedings of the Optical Fiber Communication Conference, 2015.

K. Worhoff, C. G. H. Roeloffzen, R. M. de Ridder, A. Driessen, and P. V. Lambeck, "Design and application of compact and highly tolerant polarization-independent waveguides," IEEE J. Lightw. Technol., vol. 25, No. 5, pp. 1276-1282, May 2007.

S. K. Selvaraja, W. Bogaerts, P. Absil, D. Van Thourhout, and R. Baets, "Record low-loss hybrid rib/wire waveguides for silicon photonic circuits," Group IV Photonics (2010).

D. Vermeulen, S. Selvaraja, P. Verheyen, G. Lepage, W. Bogaerts, P. Absil, D. Van Thourhout, and G. Roelkens, "High-efficiency fiber-to-chip grating couplers realized using an advanced CMOS-compatible silicon-on-insulator platform," Opt. Express 18(17), 18278-18283 (2010).

D. Vermeulen, S. Selvaraja, P. Verheyen, P. Absil, W. Bogaerts, D. Van Thourhout, and G. Roelkens, "Silicon-on-Insulator polarization rotator based on a symmetry breaking silicon overlay," IEEE Photonics Technol. Lett. 24(5), 482 (2012).

A. Mekis, A. Dodabalapur, R. Slusher, and J. D. Joannopoulos, "Two-dimensional photonic crystal couplers for unidirectional light output," Opt. Lett. 25(13), 942-944 (2000).

L. Chen, C. R. Doerr, L. Buhl, Y. Baeyens, and R. A. Aroca, "Monolithically integrated 40-wavelength demultiplexer and photodetector array on silicon," IEEE Photonics Technol. Lett. 23(13), 869-871 (2011).

C. R. Doerr, L. Chen, D. Vermeulen, T. Nielsen, S. Azemati, S. Stulz, G. McBrien, X.-M. Xu, B. Mikkelsen, M. Givehchi, C. Rasmussen, and S. Y. Park, "Single-chip silicon photonics 100-GB/s coherent transceiver," in Optical Fiber Communication Conference, (Optical Society of America, 2014), Th5C. 1.

M. Izutsu, S. Shikama, and T. Sueta, "Integrated optical SSB modulator/frequency shifter," IEEE J. Quant. Electron., vol. 2, No. 11, pp. 2225-2227, 1981.

D. Taillert, H. Chong, P. I. Borel, L. H. Frandsen, R. M. D. L. Rue, and R. Baets, "A compact two-dimensional grating coupler used as a polarization splitter", IEEE Photon. Tech. Lett., vol. 15, pp. 1249-1251, 2003.

R. Nagarajan and Others, "10 Channel, 100Gbit/s per Channel, Dual Polarization, Coherent QPSK, Monolithic InP Receiver Photonic Integrated Circuit", Optical Fiber Communication Conference Proceedings, p. OML7, 2011.

N. Dupuis, C. R. Doerr, L. Zhang, L. Chen, N. J. Sauer, P. Dong, L. L. Buhl, and D. Ahn, "InP-based comb generator for optical OFDM," J. Lightw. Technol., 2011.

S. Chandrasekhar and Xiang Liu, "Enabling Components for Future High-Speed Coherent Communication Systems", Optical Fiber Communication Conference Tutorial, 2011.

* cited by examiner

INTEGRATED PHOTONIC CHIP WITH COHERENT RECEIVER AND VARIABLE OPTICAL DELAY FOR IMAGING, SENSING, AND RANGING APPLICATIONS

RELATED APPLICATION SECTION

The present application is a non-provisional application of U.S. Provisional Patent Application Ser. No. 63/024,478 filed May 13, 2020 and entitled "Integrated Photonic Chip with Coherent Receiver and Variable Optical Delay for Imaging, Sensing, and Ranging Applications" and is also a non-provisional application of U.S. Provisional Patent Application Ser. No. 63/024,569 filed May 14, 2020 and entitled "Integrated Photonic Chip with Coherent Receiver and Variable Optical Delay for Imaging, Sensing, and Ranging Applications". The entire content of U.S. Provisional Patent Application Ser. Nos. 63/024,478 and 63/024,569 are herein incorporated by reference.

The section headings used herein are for organizational purposes only and should not to be construed as limiting the subject matter described in the present application in any way.

INTRODUCTION

Optical measurement systems, including, for example, interferometric optical systems represent an important approach to obtain imaging, sensing, and/or ranging information about a target or a sample. There are many medical and non-medical needs for performing optical imaging or sensing of a sample (e.g. human organ or other samples in hard to reach places). There are also many applications for systems that are capable of obtaining range or other information about a target (e.g., as a quality or feedback sensor for three-dimensional (3D) printing and additive manufacturing, general purpose on-line or off-line nondestructive examination/nondestructive test (NDE/NDT), and for light detection and ranging (LiDAR)).

BRIEF DESCRIPTION OF THE DRAWINGS

The present teaching, in accordance with preferred and exemplary embodiments, together with further advantages thereof, is more particularly described in the following detailed description, taken in conjunction with the accompanying drawings. The person skilled in the art will understand that the drawings, described below, are for illustration purposes only. The drawings are not necessarily to scale; emphasis instead generally being placed upon illustrating principles of the teaching. The drawings are not intended to limit the scope of the Applicant's teaching in any way. It should be understood that many of the figures described in the following paragraphs are drawn to illustrate concepts and embodiments of the present teaching, but are not necessarily drawn to scale and often they are simplified drawings omitting known structural and functional elements and/or simplifying optical beam propagation in a way that is known to those skilled in the art.

DESCRIPTION OF VARIOUS EMBODIMENTS

Figure 1:
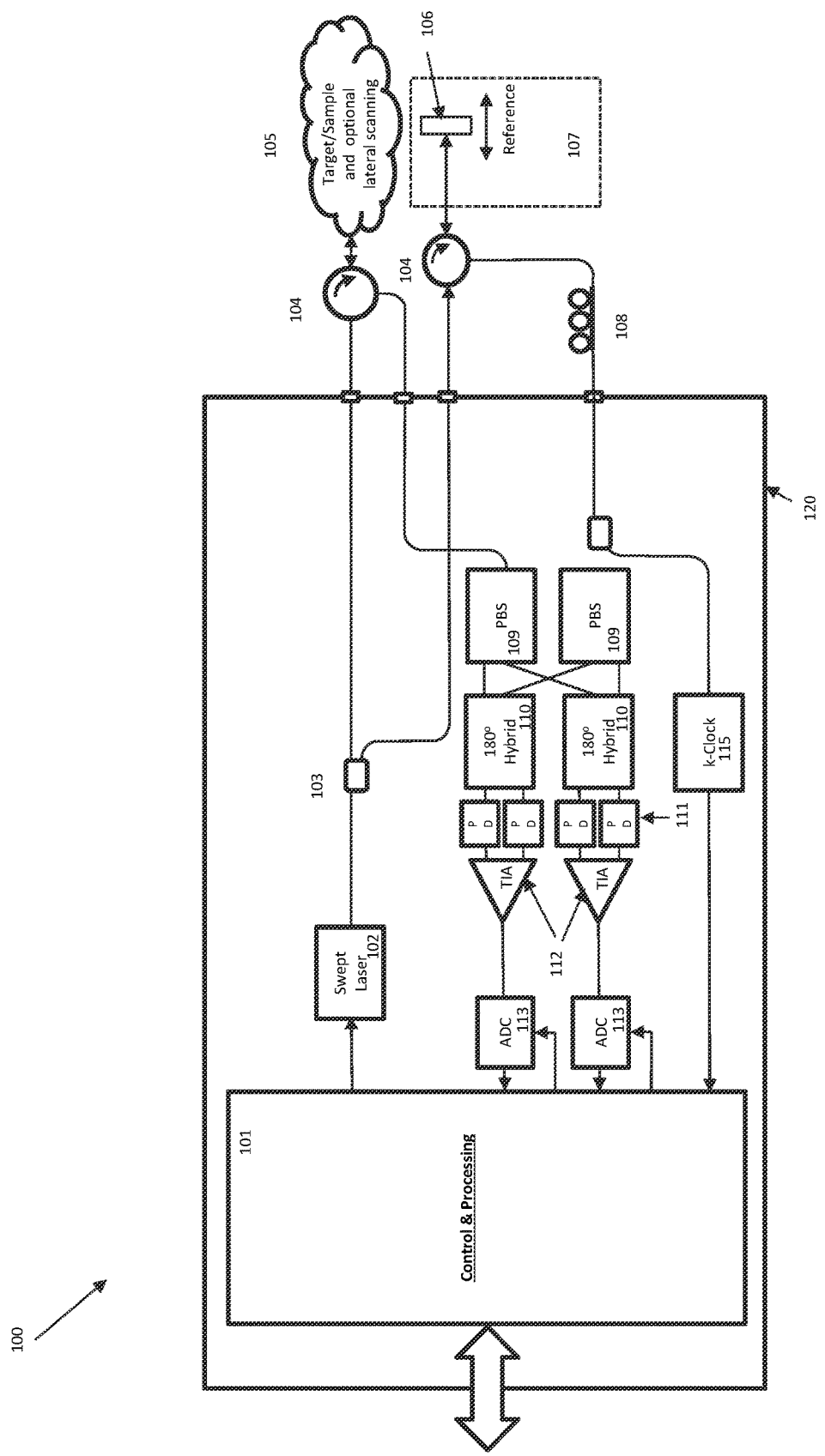
FIG. 1 illustrates a simplified block diagram of a known swept source OCT (SS-OCT) imaging system.

The present teaching will now be described in more detail with reference to exemplary embodiments thereof as shown in the accompanying drawings. While the present teaching is described in conjunction with various embodiments and examples, it is not intended that the present teaching be limited to such embodiments. On the contrary, the present teaching encompasses various alternatives, modifications and equivalents, as will be appreciated by those of skill in the art. Those of ordinary skill in the art having access to the teaching herein will recognize additional implementations, modifications, and embodiments, as well as other fields of use, which are within the scope of the present disclosure as described herein.

Reference in the specification to "one embodiment" or "an embodiment" means that a particular feature, structure, or characteristic described in connection with the embodiment is included in at least one embodiment of the teaching. The appearances of the phrase "in one embodiment" in various places in the specification are not necessarily all referring to the same embodiment.

It should be understood that the individual steps of the methods of the present teaching can be performed in any order and/or simultaneously as long as the teaching remains operable. Furthermore, it should be understood that the apparatus and methods of the present teaching can include any number or all of the described embodiments as long as the teaching remains operable.

One challenge with interferometric based systems is miniaturization to make them more compact and robust and to have lower cost and better performance for customers to integrate into their end products and applications. In order to meet this challenge, better system performance is needed as well as improved capability of various optically integrated platforms and associated components. The present teaching describes techniques, designs, and/or methods of an optical measurement system that can include aspects of photonic integrated circuits coherent receivers and/or a variable optical delay that can be used for sensing, imaging, and/or ranging applications.

There are a variety of interferometric optical system approaches to obtain imaging, sensing, or ranging information about a target or sample. These include, for example, time-domain (TD-OCT), spectral-domain (SD-OCT), and swept-source (SS-OCT) optical coherence tomography systems and other types of interferometric or non-interferometric systems. Interferometric optical measurement systems typically include a sample path and a reference path. However, it is understood that other terms may be applied to describe the two (or more) paths that are used to form the interferometer. For example, in an OCT system, there is typically a sample path and a reference path. The paths can be separate or overlapping in places. Further, it is also noted that much of the discussion below including embodiments shown in several figures are in the context of a Swept-Source OCT (SS-OCT) system. It should be understood that the variable delay line and related concepts are equally applicable to spectral-domain OCT (SD-OCT), or time-domain OCT (TD-OCT) or many other types of interferometric (or even non-interferometric) imaging, range, and sensing systems. Further, there are a wide variety of interferometric embodiments for such systems involving various types of interferometers and various types of modalities for variable delay lines including pass-through and reflective (or double pass) configurations applicable to the present teaching as understood by those skilled in the art.

One feature of the present teaching is that it addresses another challenge with some types interferometric based systems that is matching paths in the arms of the interferometer(s) that are part of the measurement system. In these systems, a relative path length between the two arms needs to be approximately matched to within the measurement range of the system. The measurement range can be, for example, a few mm to a few centimeters, or even a meter or beyond. In addition, there can be variation in the absolute and relative path lengths due to manufacturing tolerances, environmental changes, motion of the system or part of the system or the target, etc.

To accomplish the matching of the path lengths, particularly the variability, of the sample and reference arms, most prior art OCT systems use at least one of a mechanical translation stage, lenses, mirrors, and free space optic to obtain changes in the relative path lengths in the two arms and compensate for the variability. In addition, some types of automated or manual algorithms are applied to control the positions of these devices to nominally match the path lengths to within the desired measurement range. This type of variable delay may be placed in the sample arm, the reference arm, or both the sample arm and the reference arm. The element or combination of elements that provide this variable delay may be referred to as a variable delay line (VDL). This VDL provides the variable delay between the two arms of the interferometer that is necessary to match their path lengths as required by the system. The VDLs may be pass through (one-way) devices or operate in reflection (double-pass) devices.

The range required for the variable delay in, e.g., the reference arm depends on the particular application. For example, in ophthalmic OCT applications, to accommodate the range in human axial eye length, approximately 15 mm of adjustable range in the reference arm is required. In addition to this required range, there may be variability in the distance from the ophthalmic OCT system patient interface unit (where there is often a chin rest for the patient) and the patient. There may also be variability in the path length of the various optical components and fibers within the system/console. As a result, often more range than that needed to accommodate the range in the human axial eye length is typically built into the OCT variable delay line. For example, a range of 25 mm in the VDL is not uncommon.

Similarly, in endoscopic and cardiovascular OCT systems there is a variability in the length of the catheters or endoscopes that arises during manufacturing processes. This variability may be accommodated by an appropriate VDL. There may also be variability within optical components within various measurement systems that can be accommodated using a VDL. It is not uncommon for known optical measurement systems to include from 25 mm to as much as 100 mm of VDL in endoscopic and/or cardiovascular applications.

Descriptions of the various embodiments of the present teaching use various terms for a variable delay module, at least in part because different applications in the art tend to use different terminology. For example, depending on the application, a variable delay module can be referred to as a variable delay module, variable delay line, delay module, and variable delay line unit.

One feature of the present teaching is the recognition that, in addition to the examples provided above, temperature changes and/or other environmental effects can cause the relative path length distance between the two arms (e.g. sample and reference path) to change. These effects can occur during the measurement itself. For example, the relative path length distance can change during a cardiovascular pullback imaging procedure in SS-OCT when the catheter is pulled back along its longitudinal axis while the light is scanning the tissue from a spinning fiber or a spinning distal motor. This process produces helical like scans and 3D images of the lumen as is known in the art. A changing relative path length distance during a measurement process may degrade the image because the effects of a relative path length distance change caused by temperature and/or environmental artifacts can be hard to separate out from the effect of real variations in the tissue or sample being measured.

To prevent, reduce, or thwart these temperature and/or environmental factors from degrading the imaging information, a distal fluidical may be used. For example, a reflection from the inner or outer surface of the transparent sheath or window at the distal end of the catheter, or part of the distal optics, or surface of the target/sample itself can be tracked as each A-scan is performed (or several A-scans can be processed and averaged). The variable delay line is adjusted during the pullback procedure to compensate for the changing path length. Alternatively, the variation in the sample arm during pullback can be made in software or a combination of physical VDL and software adjustment can be performed. Such an approach creates a more stable image in which the temperature and environmental path length effects not associated with the tissue sample are mitigated. This type of compensation can be beneficial for many other medical and non-medical applications of OCT and interferometric imaging and ranging and sensing applications.

Known approaches to mitigating the effects of path length differences between two arms of an interferometric optical measurement system have numerous limitations. For example, some limitations include: (1) the cost associated with the VDL mechanism (e.g. a costly stepper motor based linear translation stage); (2) the cost and size and reliability associated with the mechanical, electrical, and software complexity supporting and fixturing the VDL; (3) the cost and alignment of free space optical elements such as lenses, mirrors, mechanical mounts, and retroreflectors within the VDL system; (4) the finite speed at which the mechanical system can move; and/or (5) the time-to-market lost while system vendors integrate the VDL unit with the rest of their system.

The present teaching provides a system and method for providing variable delay in optical interferometric measurement systems with significant advantages over VDL used in known OCT and other types of high-resolution interferometric imaging systems. One advantage is that embodiments of the system and method of the present teaching can have lower cost, can be more compact, and/or can allow faster time-to-market for customers to integrated than known systems and methods. Furthermore, embodiments of the system and method of the present teaching can be better able to meet the stringent requirements of high sensitivity, high-dynamic range imaging and sensing, and ranging systems based on OCT and/or other interferometric imaging approaches.

Although much of the description of embodiments of the system and method of the present teaching herein are presented in terms of a SS-OCT imaging engine or imaging system, it should be understood that the concepts are applicable to numerous optical interferometric measurement systems, including, for example, SD-OCT, TD-OCT, and other types of interferometric optical systems. Also, most of the description herein is presented in terms of a pass-through (one-way) VDL. However, it should be understood that the concepts are equally applicable to a reflective (double-pass) device). Many optical interferometric systems can benefit from the photonic integration and variable delay modules of the present teaching.

Referring now to the figures and to the associated description, it should be understood that references to OCT imaging should be understood to include, for example, 1D axial (so called A-Scans) imaging, 2D and/or 3D imaging, or enface imaging or other types of interferometric based sensing, ranging, or imaging. Also, it should be understood that references to a sample should be understood to include a wide range of things, for example, from biological tissue to non-biological specimens.

FIG. 1 illustrates a simplified block diagram of an example of a known swept source OCT (SS-OCT) imaging system 100. There are many types of known SS-OCT systems and topologies in addition to the topology shown in FIG. 1. The SS-OCT imaging system 100 includes a dual-balanced dual polarization receiver.

Swept source OCT imaging systems are known in the art so only a brief high-level discussion on how a SS-OCT system 100 works is provided. The SS-OCT imaging system 100 includes a control and processing unit 101 that includes components for computation, storage, display, and/or communication within and external to system 100. There is a swept laser 102 that can adjust its output frequency or wavelength in a repetitive fashion so as to obtain information about the sample as is well known in the art of OCT. The laser 102 generates light that is provided to an optical splitter 103 that directs the light to a sample along a sample path, and to a reference path. Along the sample path and also the reference path, there may be Faraday circulators, 104, and/or other components (e.g. fiber beamsplitters/couplers to replace the circulators) to aid in directing the light in the forward and reverse directions such as shown. Light from the swept laser 102 is directed to the sample 105 and light reflected from the sample 105 is directed back to the receiver section containing components, such as one or more polarization beam splitters 109, 180-degree optical hybrids 110, photodetectors 111, transimpedance amplifiers 112, and analog to digital converters 113. Light is also sent from the swept laser 102 to the reference arm that contains a VDL unit 107. The VDL unit 107 is shown in simplified form by the dotted box that represents the VDL unit 107. The essential ingredients included in the VDL unit 107 can include mirrors (e.g. mirror 106), or retroreflectors coupled to a linear translation mechanism along with other optical elements like lenses, fiber, etc. These devices are illustrated schematically by the two-way arrow labeled reference. It is possible to use a retroreflector on axis or off-axis, with or without a circulator 104, to create variable delay as is known in the art of variable delay line subsystems. It is also possible to use a one-way (pass-through) VDL.

The swept source imaging system 100 can include a polarization controller 108 in the reference arm path (or in the sample path, not shown) to ensure that reference arm light approximately illuminates each arm of the polarization-diversity dual-balanced receiver shown with equal powers (and avoids a null power in one of the two polarization arms). The polarization controller helps maintain good interferometric detection of the light received from the signal path and the reference path by ensuing proper alignment of the relative polarizations and optical components in the receiver path.

Optionally, the SS-OCT imaging system 100 can include a k-clock module 115 to help ensure that the sample from an analog to digital converter (ADC) 113 approximately equals frequency increments and/or repeatable frequencies as is known in the prior art.

When the laser frequency (or wavelength) of the swept laser 102 is swept in time, the light that travels the path from the swept laser to the sample and then to the receiver. At the receiver the light optically interferes with light that travels from the laser to the reference to the receiver. If the optically interfered received light has a modulation bandwidth that is within the detection bandwidth of the electronics (e.g., the transimpedance amplifier (TIA), and analog to digital converter (ADC) etc.), the electronically detected interference signal will contain amplitude and depth and other information encoded in the amplitude and frequency and phase of the detected electronic waveform. Processing the resulting waveform yields information about the sample such as its optical reflectivity profile, range, birefringence, absorption, scattering, absorption characteristics, blood flow, and/or other properties. One-dimensional images can be collected for each sweep of the swept laser 102. These are often referred to as A-scans. Two- and three-dimensional images are obtained by adding lateral scanning or rotational scanning and/or pullback scanning. The lateral scanning can be implemented at the distal, or sample, end of the probe were a target/sample and/or optional lateral scanning mechanisms 105 are included. This includes, for example, optics to transfer light to and from single mode fibers to free space and the sample.

One of the central points of FIG. 1 is to illustrate the variable delay line unit 107. This unit 107 is external to the optical measurement system engine 120. The engine is shown as a box indicated by lines 120. The engine 120 is sometimes referred to as an OCT A-scan engine or OCT imagine engine. Also, external to the engine 120 is a polarization controller 108.

Figure 2A:
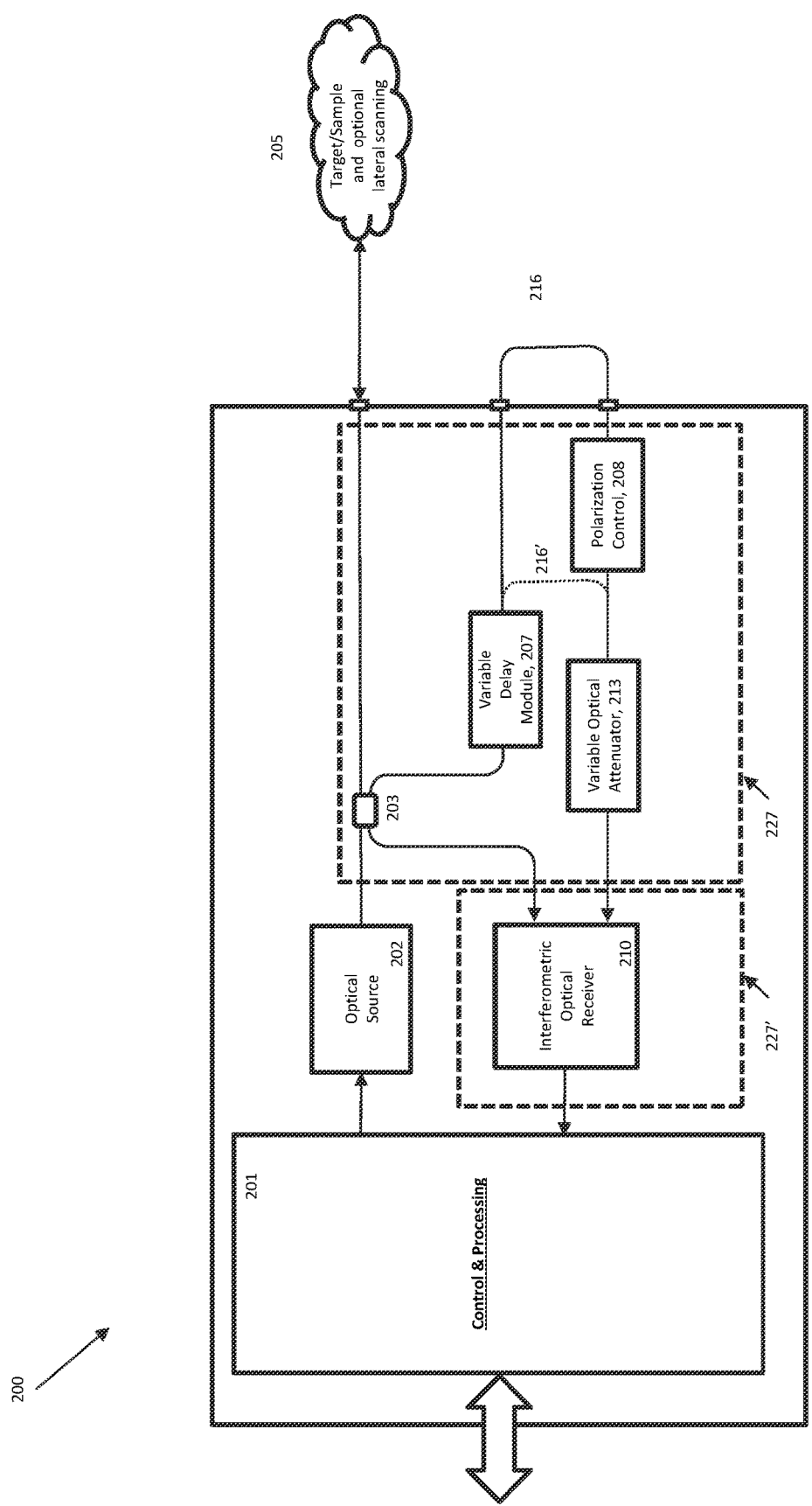
FIG. 2A illustrates an embodiment of a simplified block diagram of an interferometric optical measurement system containing an integrated photonic circuit including a variable delay module of the present teaching.

FIG. 2A illustrates an embodiment of a simplified block diagram of an interferometric optical measurement system containing an integrated photonic circuit including a variable delay module of the present teaching. The interferometric optical measurement system includes a control and processing module 201 in communication with an optical source 202 and an interferometric optical receiver 210. The control and processing module 201 also can optionally communicate with a variable delay line module 207, polarization controller 208, and variable optical attenuator 213, although these connections are not explicitly shown in FIG. 2A. The control and processing module 201 also can communicate externally to provide information about a sample 205 (e.g., an image of the sample) to an external host (not shown) and collect control information from the host. In some embodiments, the host, or the control and processing unit 201, can control the targeting and collection of light onto and from a sample 205. Optional lateral scanning capabilities for the sample 205 can also be included in the measurement system and be controlled by the control and processing module 201 and/or the host.

A sample arm path is shown as a simple path from an optical source 202, through optical coupler 203 to the sample 205, then light from the sample travels back through coupler 203 and into an interferometric optical receiver 210. This sample path is a simplified path and the present teaching contemplates many other possibilities for the sample path as understood by one skilled in the art. For example, the sample path could be in transmission and not reflection (as illustrated). The sample path could pass through additional optical elements including, for example, circulators, polarization beam splitters, quarter wave plates, and/or other types of optical devices. In operation, the light from the source 202 is coupled to sample 205 where the light is altered by some properties of the sample and then directed back to the interferometric receiver 210. The interferometric receiver can be, for example, a spectrometer used in a SD-OCT system or a coherent receiver used in a SS-OCT system. As a result of the alteration of the light by the sample, the light that is coupled from the sample 205 contains information about the sample.

A reference path shown is from the source 202 through coupler 203 to variable optical delay (VDL) module 207 to external path 216, to a polarization controller 208, to a variable optical attenuator 213, and then to the interferometric optical receiver 210. There are a wide variety of other possible reference arm configurations including, for example, having a VDL that works in double pass/reflection mode (not transmission mode as shown), where the external path could be placed internal to the system as shown conceptually by dotted line 216'. In some embodiments, there could be an additional 1:2 optical switch and a 2:1 optical switch (not shown) between the paths 216, 216' to allow a software configurable internal or external reference path 216, 216'. Generally, some of the light from the source 202 is coupled to the interferometric optical receiver 210 through a reference path that contains variable delay, i.e. VDL module 207.

In some embodiments, the VDL module 207 is integrated on one or more PICs, including components within the boundaries illustrated by dashed line 227. In a preferred embodiment, a single PIC illustrated by dashed line 227 may also contain one or more of the polarization controller 208, the variable optical attenuator 213, and, optionally, a polarizer (not shown) at the output of the VOA 213 or even the input to VDL, 207. The polarizer (not shown) may also be positioned elsewhere on the PIC. In some embodiments, the interferometric optical receiver is a PIC as illustrated by dashed line 227'. In some embodiments, a PIC that includes the VDL module 207 could also include some or all of the components of the interferometric optical receiver 210. For example, a spectrometer interferometric received used in a SD-OCT system or a coherent receiver used in a SS-OCT system includes multiple components, and some of these components may reside on a PIC with the VDL module (e.g. box 227) and some may reside on a separate PIC (e.g. box 227'). Alternatively, only one PIC may be used, e.g., this is shown conceptually by combining the dashed lines of 227 and 227' as a boundary of components on a single PIC. An example of an interferometric optical receiver for use in a SD-OCT system could include arrayed waveguide grating, etched reflective free space gratings, cascaded spectral slicers, and combinations of these and other approaches. The essential concept is to integrated one or more spatially wavelength dispersive elements and a detector array and associated readout electronics within element 210.

In some embodiments, the addition of a polarizer (not shown) prior to the input to a PIC-based spectrometer used in SD-OCT can be highly beneficial. This is because, in some embodiments of PIC based spectrometers, the dispersion of different frequencies or wavelengths from the source can vary based on polarization and distort the results. Having more optical elements on a single PIC can reduce optical losses, lowers manufacturing costs, and reduces size and complexity. It is also possible to have the optical source 202 either on the same substrate holding and supporting the PIC outlined by 227 or even on the same PIC as the VDL module 207.

Figure 2B:
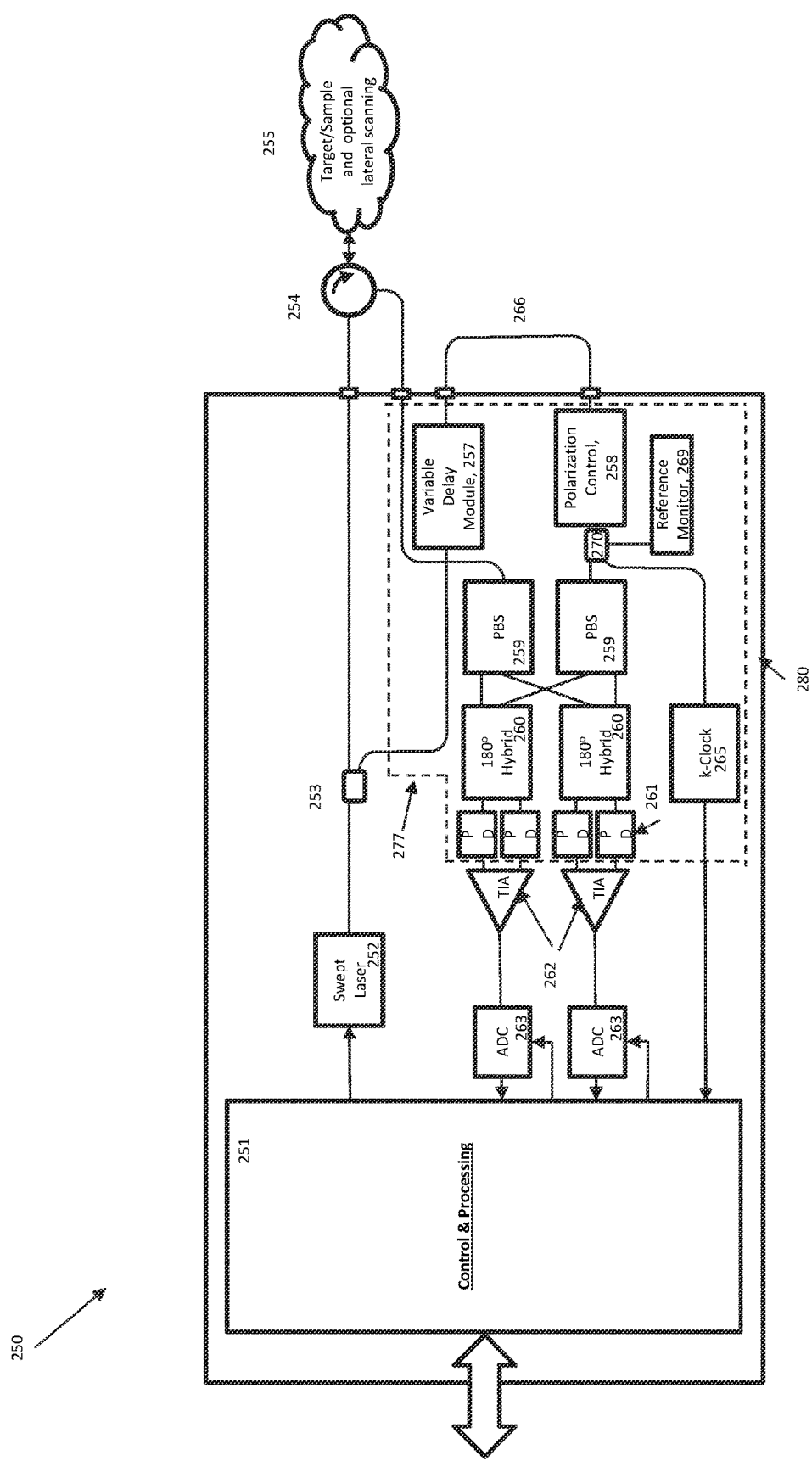
FIG. 2B illustrates an embodiment of a simplified block diagram of a SS-OCT system containing an integrated photonic circuit including a variable delay module of the present teaching.

FIG. 2B illustrates an embodiment of a simplified block diagram of a SS-OCT system 250 containing a photonic integrated circuit 277 including a variable delay module 257 of the present teaching. The embodiment of a SS-OCT system 250 of FIG. 2B illustrates an optional feature of the present teaching, which is the use of a polarization controller 258 internal to the engine 280. The engine 280 also contains control and processing 251 and other optical components of the system 250. One embodiment of the PIC boundary 277 is indicated by the dashed line. All or some of the electrooptical photonic components could be on a single PIC or there could be multiple PICs optically coupled. Additionally, some of these components could be external to the PIC(s) as discussed below. For example, the polarization controller 258 or the k-clock 265 could be outside the PIC boundary 277 in some embodiments. It should be noted that in some embodiments not all these functions need to be included in the PIC boundary 277 and in other embodiments additional functions could be included in PIC boundary 277.

Many of the components in FIG. 2B operate similar to or as described in connection with the SS-OCT system 100 of FIG. 1. Optical system 250 includes a control and processing unit 251. There is an optical frequency swept laser transmitter 252 that generates a light beam with a path to a sample 255. The light is altered by the sample either in direct back reflection or otherwise altered by the sample but not necessarily altered in back reflection. The altered light is then collected and sent into an interferometric receiver. This path from source to sample and back to receiver is a sample path. Often part of that light path includes single mode optical fibers and the details of how the light exits and reenters the single mode fiber and impinges and is collected on the sample and lateral or rotational scanning is not shown for simplicity.

Similarly, light from the frequency swept laser 252 has a path we will refer to as a reference path. In the particular embodiment shown in FIG. 2B, that path is from swept laser 252, to beam splitter 253, to variable delay line module 257, to external fiber path 266, to optional polarization controller 258, into the dual-balanced dual-polarization receiver includes polarization beam splitter elements, 259, 180 degree optical hybrids, 260, photodetectors 261, followed by transimpedance amplifiers 262, with optional automatic gain control and followed by analog-to-digital converters 263. The external fiber path 266 could be a simple single mode fiber patch cord or a more complex optical path. There can also be an optical power tap 270 on the reference arm path that directs light to an optional k-clock unit 265 and/or to a received optical power monitor 269. Note, in some embodiments, it is possible to eliminate the external patch cord 266 and have that delay be integrated on a PIC, or to have a 1:2 optical switch and a 2:1 optical switch (not shown) and allow for a software selection of an internal reference-arm path or an external reference arm path.

It should be noted that while FIG. 2B illustrates a SS-OCT system 250, the system and method of the present teaching are also applicable to other types of OCT systems and other types of interferometric imaging and ranging and sensing. In addition, it is possible to have multiple functions in an interferometric optical measurement device in addition to those shown and described in connection with FIG. 2B. For example, it is possible to have multiple OCT receivers on a single PIC or in a single module. Also, it is possible to have a combination of OCT and other imaging and sensing modalities such as Raman, fluorescence, NIR, imaging in the same module and/or sharing some of the same PICs.

One aspect of the present teaching is that while both the prior art system of FIG. 1 and system shown in FIG. 2B have a variable delay line unit, the variable delay line in FIG. 2B, VDL 257, is integrated on to a photonic integrated circuit (PIC) that optionally also contains some or all of the photonic components shown in the dotted line illustrating boundaries of a PIC 277. The VDL 107 of FIG. 1 is not in a PIC form, nor is it a PIC that is integrated with one or more other components of the measurement system 100.

It is worth noting that it is possible to put the VDL 257 outside the receiver PIC boundary in the dash line of 277. For example, it could be on a transmitter PIC that includes laser 252 or on a separate PIC from both the transmitter and receiver. The unique requirements for the VDL describe herein are still similar as those are discussed below. But in one preferred embodiment the VDL is on the same PIC as other components of the coherent receiver. In another embodiment, the VDL PIC is more closely coupled with the transmitter, 252, so that it operates on one polarization. In yet another embodiment the VDL is on its own separate PIC.

One aspect of the present teaching is the understanding that a variable optical delay line can be advantageously integrated on a PIC and such resulting systems have various important advantageous design features that impact the performance and/or utility of the measurement system. Using a variable optical delay line in a PIC can have numerous advantages over the prior art in that the resulting measurement system, for example, and OCT measurement system can be manufactured much less expensively, can be physically smaller, and can allow much faster time-to-market as the OCT imaging engine shown in FIG. 2A or FIG. 2B is much easier to integrate with their systems.

One skilled in the art will appreciate that, in some embodiments, the order of the elements in the optical path shown in FIG. 2B can be changed. For example, the variable delay line module could be after the polarization controller, or after patch chord 266. Also, the patch cord 266 could be eliminated or placed between coupler 253 and photonic integrated circuit indicated by the dashed line. The external patch cord could be eliminated and integrated on a PIC. The VDL 257 could also go in the sample path instead of the reference path but that has the disadvantage of introducing more loss in the sample path where signal-to-noise ratio is important. An essential point is that part or all of the photonic components that make up a VDL 257 are integrated onto a single PIC. Or in one important embodiment, all of the photonic components that make coherent receiver and a VDL 257 are integrated onto a single PIC illustrated by dashed line 277.

The patch chord 266 could be a simple single mode fiber or could contain other devices and materials to help balance the chromatic dispersion between the reference path and the sample path. For example, in ophthalmic applications part of the sample path goes through single mode fiber as the light goes from the system console to the patient interface where the patient rests his or her head on a chin rest, then the light goes into free space control by bulk optical lenses, then the light goes into the patient's eye traveling through the cornea, aqueous, lens, vitreous, and onto the retina. The nominal delay and dispersion characteristics on this sample path can be mitigated by putting devices with similar characteristics in the reference arm in addition to a simple single mode fiber patch cord. Or these differential chromatic dispersion characteristics can be compensated for in the electronic dispersion compensation processing, that can be performed in the control and processing module 251 or elsewhere, or there can be a combination of both dispersion mitigation approaches.

At first it might appear that polarization maintaining (PM) fiber could be used in the patch cord 266 of FIG. 2B so that the polarization controller 258 can be eliminated. However, alignment is an issue as it is very difficult to launch the light at exactly the correct angle. Also, there is often cross talk between the fast and slow axis of a polarization maintaining fiber. The differential velocity inherent in polarization maintaining fiber leads to multipath interference with degrades signal quality. In some embodiments, PM fiber can be used and the polarization controller 258 is eliminated. Polarizing fiber can also be used in some applications. It is also possible to put the polarization controller 258 on or nearer the swept laser 252 (which can be a PIC) where the input polarization may be more defined. This would be the case, for example, for lasers that emit a fixed polarization.

In other applications with more stringent multipath requirements, a single mode fiber and a polarization controller are used. The polarization controller 258 shown in FIG. 2B can be an integrated photonic endless (i.e. reset free or non-reset free) polarization controller. A variety of known approaches for integrated photonic polarization controllers can be utilized. Many of these known polarization controllers have been developed for optical telecommunication systems.

One large difference in requirements for OCT systems, as compared, for example to telecommunication systems, is the need for simultaneous broad optical bandwidth (e.g. ~100 nm for OCT systems and ~1 nm for telecom systems), and also extremely low multipath interference. Equally important is polarization controller does not necessarily have to be able to span the whole Poincare' sphere of input polarizations to output polarizations since, in dual-polarization OCT systems such as depicted in FIG. 2B, it is sometimes only required to have approximately equal powers hitting the two receivers that represent each polarization and the exact phase can be less important. The polarization controller can be reset-free or, in many embodiments, this is not required since the polarization can be adjusted before measurements begin. In some OCT applications such as polarization sensitive OCT a more capable polarization controller can be used to map tissue birefringence. Furthermore, for some embodiments of polarization controllers, the output can deliver the TE and TM light in two separate waveguides which can eliminate the requirement for the reference arm PBS. This has the advantage that only one mode of polarization needs to be routed around the PIC simplifying designs of waveguide-based splitters, combiners, hybrids, etc.

There are known approaches and methods for providing variable optical delay lines. Many of these known approaches are associated with trying to achieve true time delays for RF phased array process. Some approaches have even been demonstrated in integrated photonic devices or combinations of integrated photonics and optical fibers. There are even known systems that use optical time delays in low coherence interferometry and OCT. But these known systems and approaches do not meet the required combination of needs of a large optical bandwidth (~100 nm), high-sensitivity systems (~100 dB), high-dynamic range (>50 dB), sufficient low loss, sufficiently low multipath, sufficiently fine minimum step size, and/or sufficiently long delay solution that can be integrated in a small low-cost easy to integrate module such as can be used in state of the art OCT and other interferometric imaging, ranging, and sensing system. This shortfall in the known systems is addressed by the variable optical delay system and method and interferometric measurement using variable optical delay system and method of the present teaching.

There are a variety of ways to implement a VDL on a PIC and variety of important design requirements or inputs. One particular design input is the required range. As discussed above, typical commercial OCT systems have VDL units that range from 15 mm to 100 mm. It should be noted that the path length along the sample path is typically much bigger than 15 mm to 100 mm. For example, in intravascular OCT systems the catheter alone can be more than one-meter long. The SS-OCT system architecture in FIG. 2B accounts for this by the use of patch cord 266. The nominal different delay between the sample arm and the reference arm can in large part be compensated using this patch chord. Further that patch cord can easily be changed to accommodate different types of systems (e.g. a cardiovascular system, endoscopic system, or ophthalmic system all have different nominal delays). Only the variable delay due to manufacturing tolerances and environmental variations and patient or sample motion needs to be compensated for in the fine tuning of the VDL unit, 257.

One feature of the present teaching is the recognition that the throughput loss of a VDL module is an important design parameter and so, too the position of the delay in the system. It is desirable to have low throughput loss since optical power should not be wasted (especially in the sample path). However, by having the PIC VDL in the reference path there is more tolerance for loss. Typically, a swept laser source can put out many tens of milliwatts, and less than ~1 mW is typically required at each receiver photodetector so the VDL unit can easily accept more than 3 dB loss if it is in the reference path where typically a 3 dB loss in the reference arm is more of a problem since it effects signal-to-noise ratio more directly.

One feature of the present teaching is the recognition of the importance of minimizing multipath. This can be especially true for applicability to use in high sensitivity high-resolution OCT systems. Multipath arises from the leakage of optical power from signals in the desired or selected path in a variable delay into non-selected paths. This leakage signal then appears at the receiver at one or more different delay times than the chosen or desired path delay. These leakage signals can be confused with real signals if they fall within a measurement range.

For example, some OCT images can span more than 50 dB in the intensity of the brightest pixels to the darkest pixels and the minimum detectable signal can be $1:10^9$ (that is, some OCT systems can detect one part in a billion of the power incident onto the sample). Thus, if the VDL unit has stray reflections or other structures that lead to echoes or polarization mode dispersion or other attributes that lead to multiple paths that are within the axial range measurement window then those echoes show up and can significantly degrade the OCT image information. Thus, it is important that multipath effects within the measurement window axial range be kept to less than 50 dB and even less is preferred. Here, the word measurement window referrers to the depth range over which sample information is collected. For example, in retinal or coronary artery imaging a range of zero to five to seven millimeters from the surface of the retina to deeper retina tissue is typical, or the exit spot of light from a catheter too deep into an artery wall, can be displayed in a zero to seven measurement window. In these instances, a multipath effect from the VDL that shows up at 25 mm when the measurement range is only between zero and seven millimeters will have far less effect and far less visibility on the image. That is because these multipath effects can be electrically filtered out of the image or data.

One feature of the present teaching is the recognition that photonic integration can help produce long optical path delays with desirable characteristics for variable delay modules for interferometric sensing systems. One way to achieve a long optical delay using an integrated photonic circuit is to have a long waveguide, which is tightly spiraled fabricated on the integrated photonic circuit. The long optical delay can be made variable if the waveguide temperature is controlled using thermal heating/cooling to tune the path length of light propagating through the waveguide based on the known optical path length dependence on temperature. Thus, the optical path length of the waveguide is controlled using temperature. Known systems that use thermal control to produce a particular waveguide path length have a limitation in that even with a long waveguide and large variable heating power applied, the total variable delay of the optical path length is small and can can have excessive optical loss and taking up large portions of PIC area. Another disadvantage of this approach is that, in some designs, it is not very fast and speed can be needed as mentioned above in the example of intravascular OCT pullback which occurs ~1 s. This approach has the advantage in that it can have virtually no minimum step size.

Figure 3:
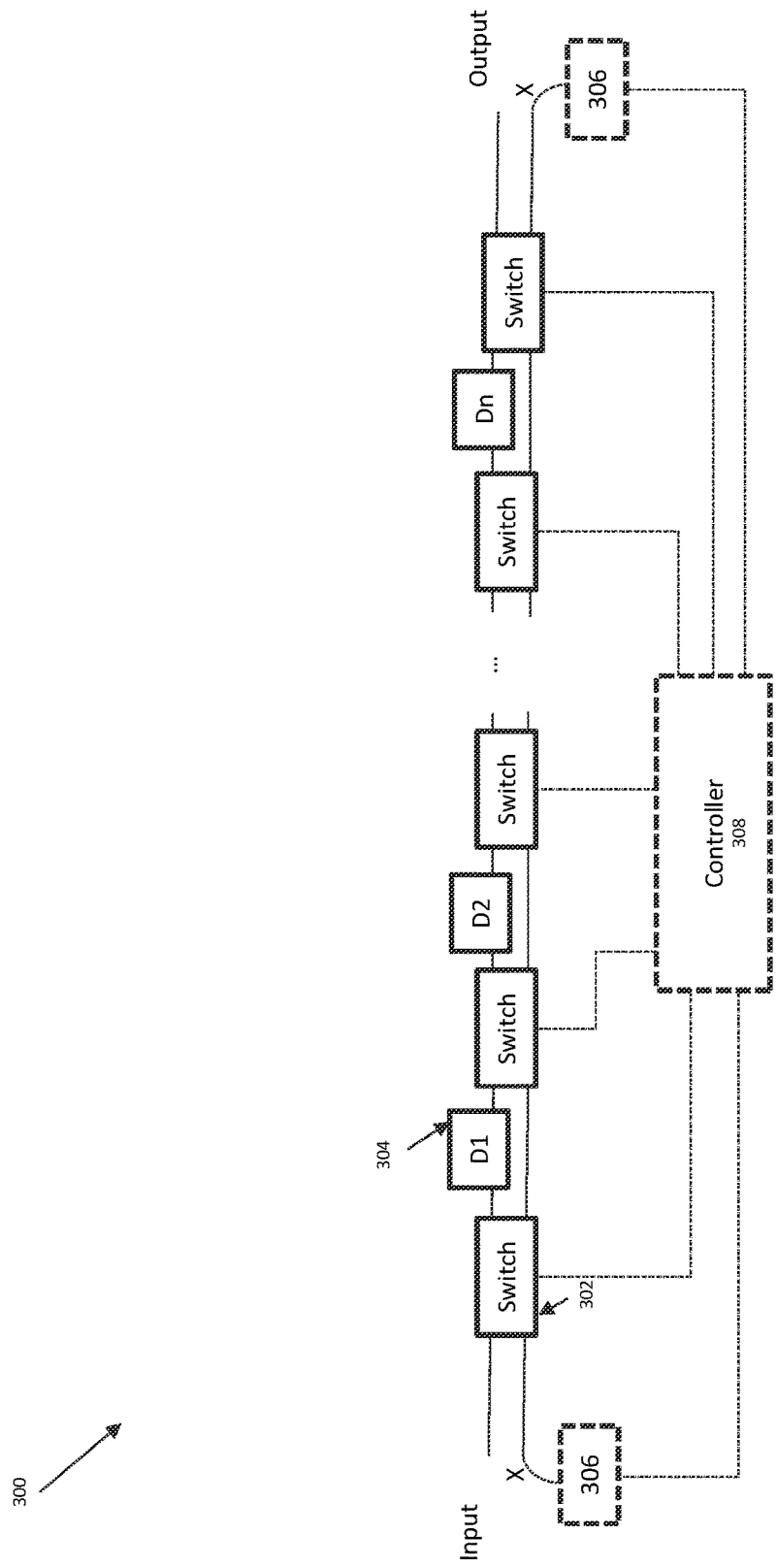
FIG. 3 illustrates an embodiment of a simplified block diagram of a variable delay module using a cascade of two-by-two switches of the present teaching.

A better approach that can be implemented on a photonic integrated circuit is shown in FIG. 3. FIG. 3 illustrates an embodiment of a simplified block diagram of a variable delay line module 300 using a cascade of two-by-two switches 302 of the present teaching. Here is shown a linear set of 2×2 integrated optical switches 302. Each switch 302 allows connection from a desired input to one of two paths: one path leads directly to the next switch stage, and the other path leads also leads to a second input of the next stage but after an additional delay 304. The delay 304 for the first stage is D1, and the delay difference for the next stage is D2, and so on. This delay is the difference between an optical path length from the output connected to the delay 304 and the optical path length from the second output to respective inputs of the switch 302 at the next stage. The delay 304 can simply be a section of integrated optical waveguide. Each delay stage of the switch can be an increasing delay. For example, the first stage D1 could be 0.1 mm differential delay, the second stage D2, could be 0.2 mm. and so forth. In that case an 8-stage switch would have ~25 mm of maximum delay with a minimum increment step size of 0.1 mm. This matches nicely the requirements of many ophthalmic and cardiovascular OCT systems. Other number of stages and ratios of delays are possible and it is possible to use instead of two arms in each switch stage, a switch connecting outputs, to three or more arms. In other words, the switch is connected to three outputs at any or all of the various stages in the cascade.

It is important that all the elements of VDL 300 including the couplers a switches 302 be carefully designed to minimize loss and reflections and unused ports terminated using angled waveguides and/or absorptive doping's to prevent reflections leading to multipath effects. Switches 302 can connect to a controller 308 that can direct the switch state of each switch to select the desired path with its associated desired delay. The controller can also control characteristics of the optical properties of the switch, including, e.g. the extinction ratio of the switch state. The controller can thus help minimize leakage of light from a selected path into a non-selected path. The ports labeled "X" could be unused ports or one of them could have an optional optical power sensor 306 connected to a controller 308 to optimize the state of the switch 302. There are a variety of ways to control the switch 302 such as described herein.

A feature of the present teaching is that the elements of the variable delay line module 300, including any or all of inputs and outputs, switches 302 and delays 304, $D_j$, can be integrated onto one or more photonic integrated circuits. Using photonic integration advantageously improves control over various optical path lengths, reduces optical losses in various elements and their interconnections, reduces size, improves stability, increases electrical and optical bandwidths and provides other performance improvements. Thus, embodiments of variable delay line modules of the present teaching use one or more integrated optical switches to select a particular set of one or more optical paths to be followed in an integrated optical device in order to realize a desired delay. By selecting different sets of one or more optical paths using the one or more optical switches, different desired delays are realized.

One advantage of this staged approach variable delay line module 300 is that embodiments of the delay line module architecture, in combination with the photonic integration implementation, allow both short and long delays to be realized. For example, using the traditional approach described in connection with FIG. 1 of an external delay line on a linear translation stage with a moving mirror or retroreflector and free space optics, it would be very difficult to get a 1 m long variable delay line. But, with an integrated optic version with a one millimeter first stage, a one-meter VDL could be achieved in ~10 stages. No known commercial OCT system have this kind variable delay as the fixturing, space requirements, performance and cost would be problematic for a 1-meter delay. But, for example, an integrated optic version could fit in an area less than a several centimeters square or even less using tightly confined low-loss silicon nitride spiraled waveguides. Furthermore, a one-meter linear translation stage would have difficulty of quickly moving from one end to the other (even if there were multiple paths inside the translation stage instead of just one). In contrast, even a thermally activated VDL in integrated photonics could be fast (e.g., <1 sec) and an electrooptical switch element can be much faster (e.g., microseconds). Another advantage of the staged variable delay line 300 using photonically integrated components approach is that embodiments of the delay line module architecture, in combination with the photonic integration implementation, allow precise values of desired delays to be realized. Yet another advantage of this approach is that embodiments of the delay line module architecture, in combination with the photonic integration implementation, allows the resolution of different desired delays to be realized to be very small. That is, small selected increments of controllable delay (i.e. step size) can be realized together with long values of total delay.

There are a variety of types of integrated photonic switches that can be used to implement the switch 302. One approach is to use a Mach Zehnder type of switch as known in the art. A feature of a Mach Zehnder type of switch is that it is easily integrated into a photonic integrated circuit. In addition, numerous other known switch architectures, including those that can be fabricated on a photonic integrated circuit, can be used. Delays 304 can be provided in integrated devices using control over the optical path lengths of the integrated devices, including waveguides and other optical elements, which pass the light between the switches 302. This kind of staged variable delay architecture can be implemented without switches but rather to use a broadband coupler followed by electronically controlled absorbers (as described in connection with FIG. 7) but this has increased throughput loss and is less desirable for a large number of stages.

Figure 4:
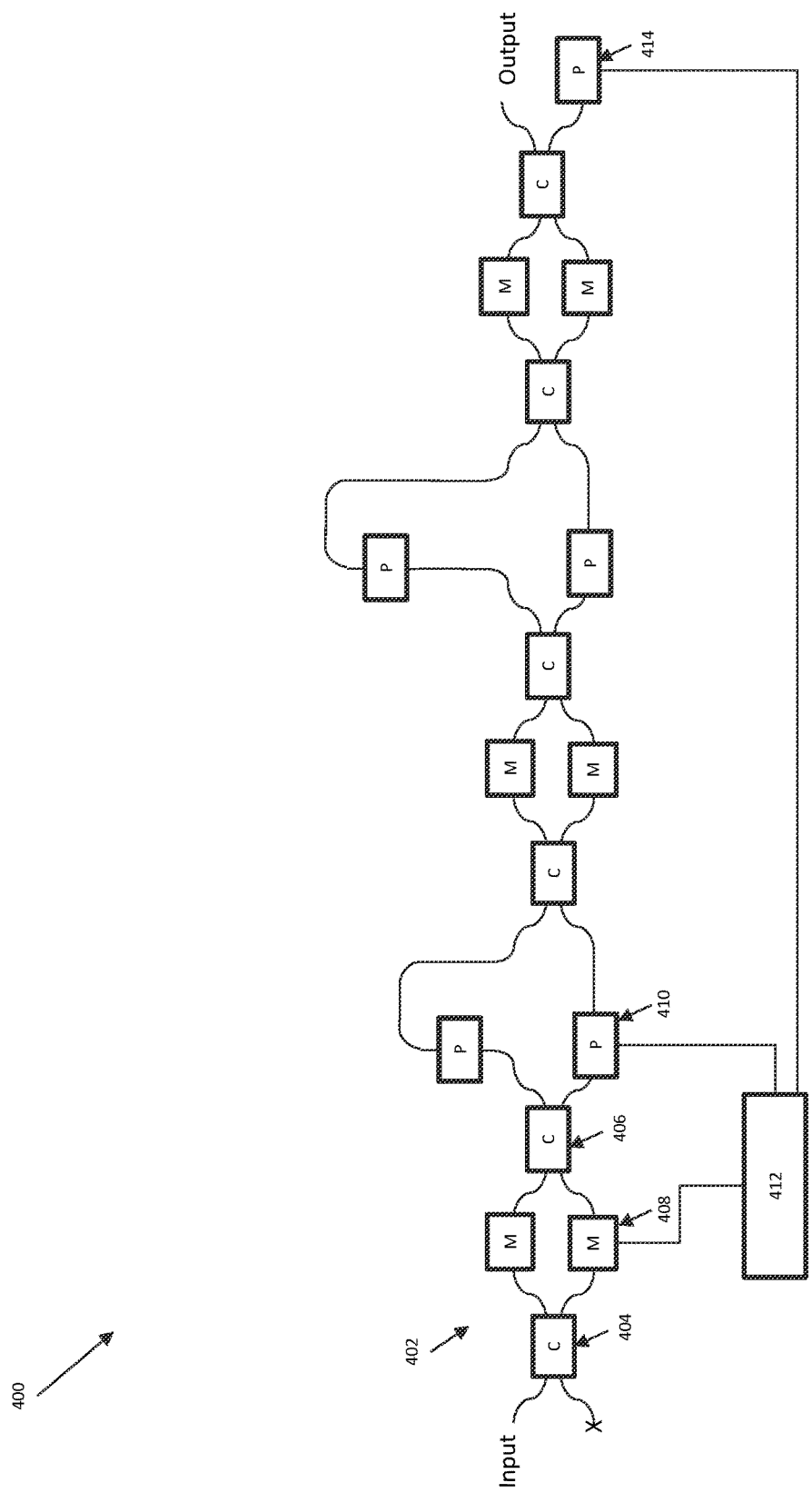
FIG. 4 illustrates an embodiment of a variable delay module including Mach Zehnder modulators that form a switch of the present teaching.

FIG. 4 illustrates an embodiment of a variable delay module 400 including Mach Zehnder modulators that form a switch 402 of the present teaching. This module 400 is an example of a two-stage discrete variable delay. Additional stages of Mach Zehnder modulator switches can (and in most preferred embodiments would) be added. Mach Zehnder switches have an input coupler 404 and an output coupler 406 and a modulator 408 in one or both arms. It should be understood that couplers are generally four port optical couplers although not all ports may be used and are indicated by C. Also, note that modulators are indicated by M and shown as in both arms. In some embodiments, one or more of the modulators 408, M, is a phase modulator. For OCT, and other broad optical bandwidth applications, it is important that the switch 402 cover a very broad spectral bandwidth to cover the entire laser source optical spectrum. The laser source optical spectrum could be a spectrum that is used for either the frequency sweep range in SS-OCT or the optical spectrum in SD-OCT and TD-OCT systems.

One feature of the present teaching is that it can accomplish providing VDL that covers a very broad spectral bandwidth to cover the entire laser or broadband source optical spectrum. In some embodiments, the length of the two arms that make up the Mach Zehnder modulator switch 402 are made to be equal, preferably equal to within less than a wavelength of the optical laser source optical spectrum. If there is a big imbalance in the length of the two arms that form the interferometric action between the two couplers 404, 406, C, of each switch stage then the resulting Mach Zehnder switch 402 will not have as broad bandwidth as possible. A big imbalance can lead to multipath interference as good switching extinction will not be achieved over the broad bandwidth of the source. In some embodiments, the couplers 404, 406 are chosen to be broadband couplers and have a splitting ratio that is nominally 50/50 over the optical bandwidth of the laser source. This will ensure good extinction is possible. In some embodiments, the phase modulator 408, M, is properly tuned to produce maximum extinction in the unwanted arm and maximum throughput in the desired arm (that is, an extinction that is as close to zero as possible) at the output of the Mach Zehnder switch 402. This above discussion can apply to any or all of the Mach Zehnder switches in the cascaded VDL module 400. The module 400 includes three Mach Zehnder switches 402, one that is used to cascade two delay stages and one input and one output optical switch.

There are a variety of types of phase modulators, M, that can be used in connection with the present teaching. This includes, for example, thermal phase modulators and/or electro-optical phase modulators. Some embodiments of the switch 402 utilize a phase modulator 408, M, in only one arm of the Mach Zehnder modulator switch 402. To achieve maximum extinction, some embodiments use an electrical signal to the phase modulator, M, that is driven to a signal level so as to achieve either zero-degree phase shift between the arms or a 180 degree (Vπ) phase shift. The required electrical drive signal level to achieve this can be calibrated and stored. The drive signal can be provided by a controller 412.

Alternatively, or in addition to calibrating and storing the required drive signal, dithering techniques (or hill climbing, null seeking, lock-in or other known techniques) may be combined with output power monitors 410 (indicated by P) that tap a small portion of the light from one or both arms can be used to determine the zero point and maximum drive point of the modulator switch. The drive level to the phase modulators M is adjusted until the signal is nulled in the non-selected arm and maximized in the other selected arm. A controller 412 can be used to monitor the power from any or all of the power monitors 410 in the delay module 400 and to adjust any or all of the phase modulators 408 for maximum extinction of a non-selected path from a switch 402 in one or more stage of the delay. The monitoring of power and control of extinction can also be used to reduce leakage of light from a path that is selected into a path that is not selected in the variable delay module 400. It should be understood that not all connections to and from the controller 412 to modulators and power monitors that can be utilized are shown in FIG. 4 for simplicity.

In some embodiments, each stage uses a different dither frequency to allow each stage to be isolated from one another while operating in parallel. The signal associated with each dither frequency is used to control the drive level for the respective Mach Zehnder modulator switch 402. In some embodiments, the dithering is applied serially, so only one stage is being adjusted or tweaked, and/or controlled, at a time. Some embodiments drive the phase modulator 408 with a sinusoidal (or other repetitive waveform) frequency and monitor the power in the nulled arm to minimize the frequency. Some embodiments maximize the second harmonic of that frequency that can occur at a null or maximum. Some embodiments use dithering or lock-in approaches to controlling the Mach Zehnder switch state to get good through put in the desired arm and maximum extinction undesired arm of each stage of the switch. Some embodiments use hill climbing to controlling the switch state to get good through put in the desired arm and maximum extinction undesired arm of each stage of the switch. Some embodiments use valley finding to controlling the switch state to get good throughput in the desired arm and maximum extinction undesired arm of each stage of the switch. For the last stage, some embodiments only monitor the unused arm with a power monitor 414 and null that monitored signal using the controller that controls one or more of the modulators 408, M. Other embodiments can use a power detector in the output arm of the last stage.

A feature of the present teaching is that the elements of the variable delay module 400, including any or all of inputs and outputs, couplers 404, 406, C, modulators 408 M, Mach Zehnder arms (e.g. optical waveguides), and power monitors 410, P, can be integrated onto one or more PICS. Using photonic integration advantageously improves control over various optical path lengths, reduces optical losses in various elements and their interconnections, reduces size, improves stability, lowers costs, and increases electrical and optical bandwidths and provides other performance improvements.

Figure 5:
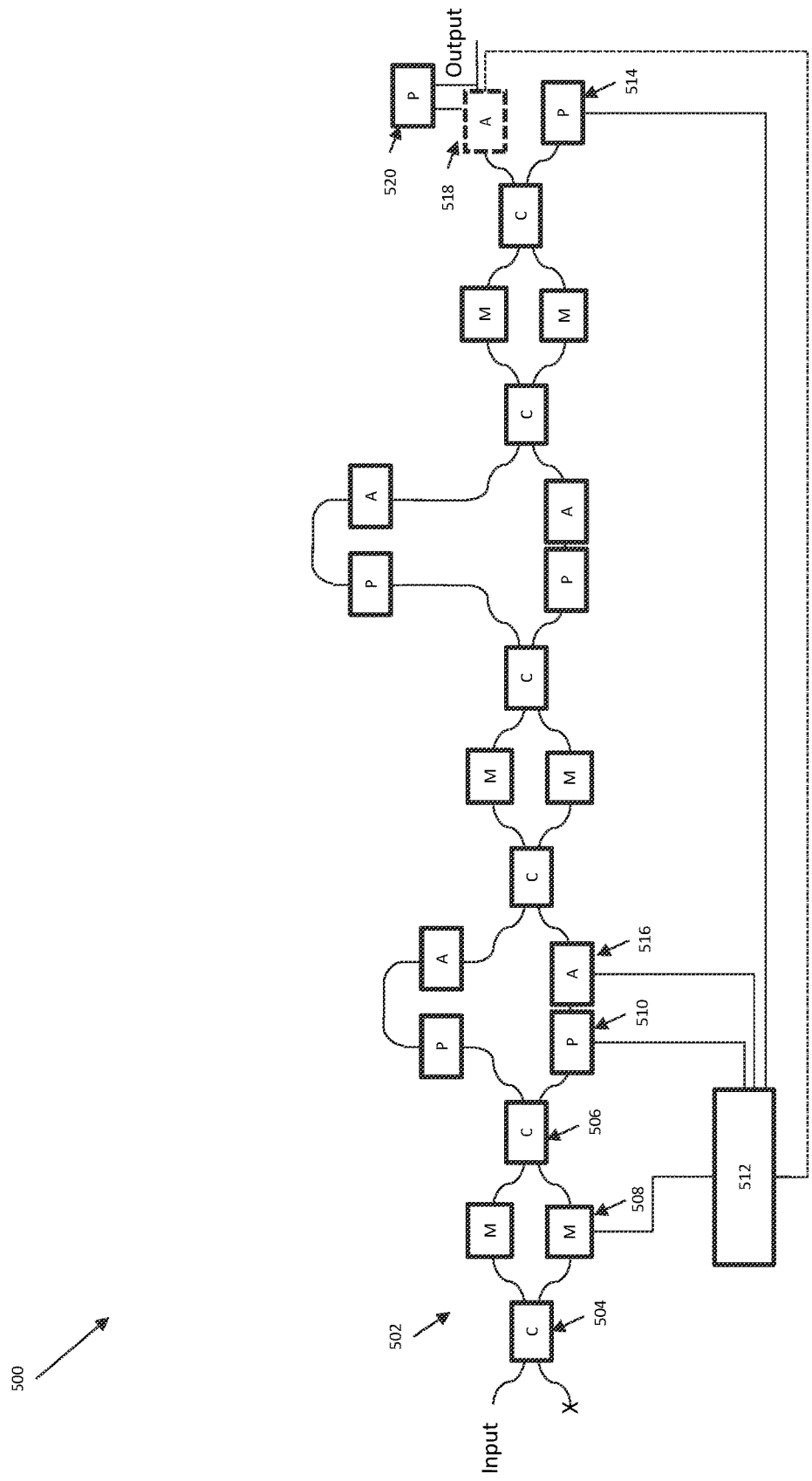
FIG. 5 illustrates an embodiment of a variable delay module including Mach Zehnder modulators with controllable loss devices in each delay arm between each stage of the present teaching.

FIG. 5 illustrates an embodiment of a variable delay module 500 including Mach Zehnder modulators 508 with controllable loss devices in each delay arm between each stage of the present teaching. This embodiment of cascaded Mach Zehnder switches 502 as a variable delay module 500 further increases the multipath extinction, by reducing the amount of optical power in a leakage signal that crosses into one or more non-selected paths as compared to a selected path. Improving multipath extinction can be important to achieve desired measurement performance in OCT and other interferometric imaging and sensing systems. The Mach Zehnder switches 502 include an input coupler 504 and output coupler 506 and a modulator 508 in one or both Mach-Zehnder arms (both arms are shown). The variable delay module 500 uses one or more additional controllable absorptive device 516, labeled A, which can be added to each output arm of each switch stage. The controllable absorptive device 516, A, may be a variable optical attenuator. Electrical signals are applied to each attenuator 516, A, by a controller 512 to achieve maximum extinction in an undesired arm and a maximum throughput in a desired arm of each stage for a particular desired switch state. The attenuators 516, A, do not need to be continuously variable in attenuation, and all or some can in some embodiments be binary devices (full on or full off).

A feature of the present teaching is that the elements of the variable delay module 500, including any or all of inputs and outputs, couplers 504, 506, C, modulators 508, M, Mach Zehnder arms (e.g. optical waveguides), power monitors 510, 514, P, and controllable attenuation devices 516, A, can be integrated onto one or more PICS. Examples of variable optical attenuators 516 include, for example, an electrooptical modulator based on carrier depletion in a doped waveguide, additional Mach Zehnder modulators, electro-absorption modulators based on semiconductor within or adjacent to the waveguides, electrooptical directional couplers, P-I-N variable optical attenuators, micro-electromechanical system (MEMS) based VOAs, and other approaches. In various embodiments, these attenuator devices may or may not be integrated onto a PIC with the other elements of the module 500.

In some applications, it can be important as the number of stages gets large, or a delay in a particular stage is large, to compensate the optical throughput loss when the VDL is set to its lowest loss state or its highest loss state. This could be the case in a large total delay line (e.g. 1 meter) or even in smaller VDLs (25 mm). Otherwise, the image or other information produced by system 250 in FIG. 2B, could get brighter or darker as the VDL delay is adjusted. In one embodiment, this high optical throughput loss can be compensated for electronically and/or in software by adjusting the transimpedance amplifier gain (if for example it contains an automatic gain control stage) or in post processing after the ADC. If each configuration of the switch loss is known (e.g. it is calibrated during manufacturing, or a calibration step prior to imaging), then as the VDL state is changed the detected signal or imaging information is correspondingly adjusted.

In another embodiment, a VDL is designed to be approximately equal loss independent of the switch state. As one example, this can be done by adding another variable optical attenuator 518 in series with the VDL 500 of FIG. 5 at the output. The VDL 500 can either calibrate for each switch state and adjust the VOA 518 accordingly, and/or put a power monitor 520 off an optical tap at the output and a feedback loop to the VOA 518 to keep the output constant.

In yet another embodiment, the loss in each arm between stages is kept near constant, and for example the attenuation or absorption "A" in the direct path is increased actively or statically in waveguide and device design to match the total loss in the longer delay path. This increase in attenuation can be a fixed amount (static) that is always present. Further the attenuation or absorption "A" in the direct (non-delayed path) between stages can consist of two components, a fixed attenuation and the variable attenuation from the additional controllable absorptive device A.

In yet another embodiment, the use of optical amplification is used to compensate loss from VDL state. In yet another embodiment, the Mach Zehnder switch state is adjusted to yield a constant power in the desired arm and the absorptive device extinguishes the undesired light in the other arm. For example, in this embodiment, it can be beneficial to switch the order of the attenuator 516, A, and power meter 510, P, from that order shown in FIG. 5. A combination of one or more of the techniques described above, or other techniques, is used to achieve a throughput loss that is mostly independent of VDL state. Note that the various embodiments described herein may use fewer or more optical components than are shown explicitly in FIG. 5 as needed for the specific embodiment.

A feature of the variable delay modules of the present teaching is that it allows the VDL to be used in a system where the sensing, ranging, or imaging information can be independent of the VDL state. An important goal to realize this feature is that a loss of the VDL is nominally the same for each value of delay and/or delay increment. That is, the output power for each value of path delay is nominally the same, or is the same to within a desired range. Another goal to realize this feature is that a loss of the VDL as a function of its optical path length is predetermined and can be used to compensate the effect of that loss in a collected measurement. These goals may be pursued independently or collectively.

Another important system design considering, for example, the SS-OCT system 250 described in connection with FIG. 2B is to accommodate any differences in chromatic dispersion in the sample and reference paths. In SS-OCT (or SD-OCT) systems, differential dispersion can degrade axial resolution and cause chirp in detected signal even to the point where the some of the signal is outside the receiver bandwidth as is known in the art. For example, in an ophthalmic application, sample arm length or delay variation can come from varying distances between the patient interface and a human placing their chin on a chin rest (resulting in more or less propagation in air) or different eye diameters (with more or less aqueous, lens, and vitreous). In an intravascular application, the catheter can be slightly longer or shorter during manufacturing. And in both cases, the components and optical fibers and optical connectors and/or patch cords that make up system 250 can be slightly longer or shorter. There are differences between the chromatic dispersion characteristics of air or eye tissue and photonic integrated optical waveguide and also in single-mode optical fiber of a catheter and photonic integrated optical waveguide. Similarly, the VDL itself can introduce a varying amount of chromatic dispersion due to the different propagation distances due to switch state.

In one embodiment, this dispersion difference is mitigated by placing optical elements in the sample arm or reference arm that compensate for this to the extent possible (at least the bulk of the fixed chromatic dispersion difference) as was mentioned above in the element of 266 of FIG. 2B (element 266 can consist of more than a simple patch cord as shown in FIG. 2B). In another embodiment, dispersion compensating optical elements can be placed in the integrated photonic waveguide structures in the VDL or elsewhere in the reference or sample path including the PIC of FIG. 2B (not shown in FIG. 2B for simplicity). In another embodiment, the chirp that results from sample and reference arm path chromatic dispersion differences is calibrated, either during manufacturing, during a calibration step prior to imaging, and/or during imaging using a fiducial with a known reflection and corrected for in electronic processing.

In another embodiment, the PIC waveguides are designed to have minimal chromatic dispersion characteristics. This can be an effective way to minimize the detrimental effects of chromatic dispersion and the imperfections in the software methods to correct for them. The lower the chromatic dispersion of the waveguides, the less the demands on a software or electronic methods for chromatic dispersions compensation in the signal processing (and such adaptive correction methods have finite ability for correction specially in low signal to noise environments) and increase computational complexity with drives cost, power, and processing delay. A combination of one or more of these or other techniques is used to achieve high axial resolution and minimal effects of chromatic dispersion mismatch independent of VDL state. One example of a method for chromatic dispersion electronic compensation is described in "Ultra-high-resolution, high-speed, Fourier domain optical coherence tomography and methods for dispersion compensation, Wojtkowski, et al, Optics Express, Vol. 12, No. 11, 2004". There are many others as known in the art.

In long VDLs, it can be difficult to design the photonic integrated structures and waveguides to have equal propagation characteristics between different polarizations (e.g. the TE and TM waves). It is important to design the structures to be as polarization independent as possible. Alternatively, the VDL can be placed in locations that only have one polarization. In one embodiment the VDL can be placed on or near the transmitter side near or on the same PIC or module as the swept laser 252 and after splitter 253 of FIG. 2B or the optical source 202 or FIG. 2A. In this case it could be a different PIC that outlined in dashed line 277 or FIG. 2B, or it could be the same PIC. In another embodiment, one (or more) VDLs can be placed after the polarization controller 258 (or 208) where the polarization controller converts the potentially arbitrary polarization received from 266 (or 216) into one or more photonic waveguides of a known polarization. It is also possible to put a polarizer at the input to the VDL to further ensure that there is little to no light in VDL configurations that are designed for single polarizations while extinguishing the unwanted polarization.

Figure 6:
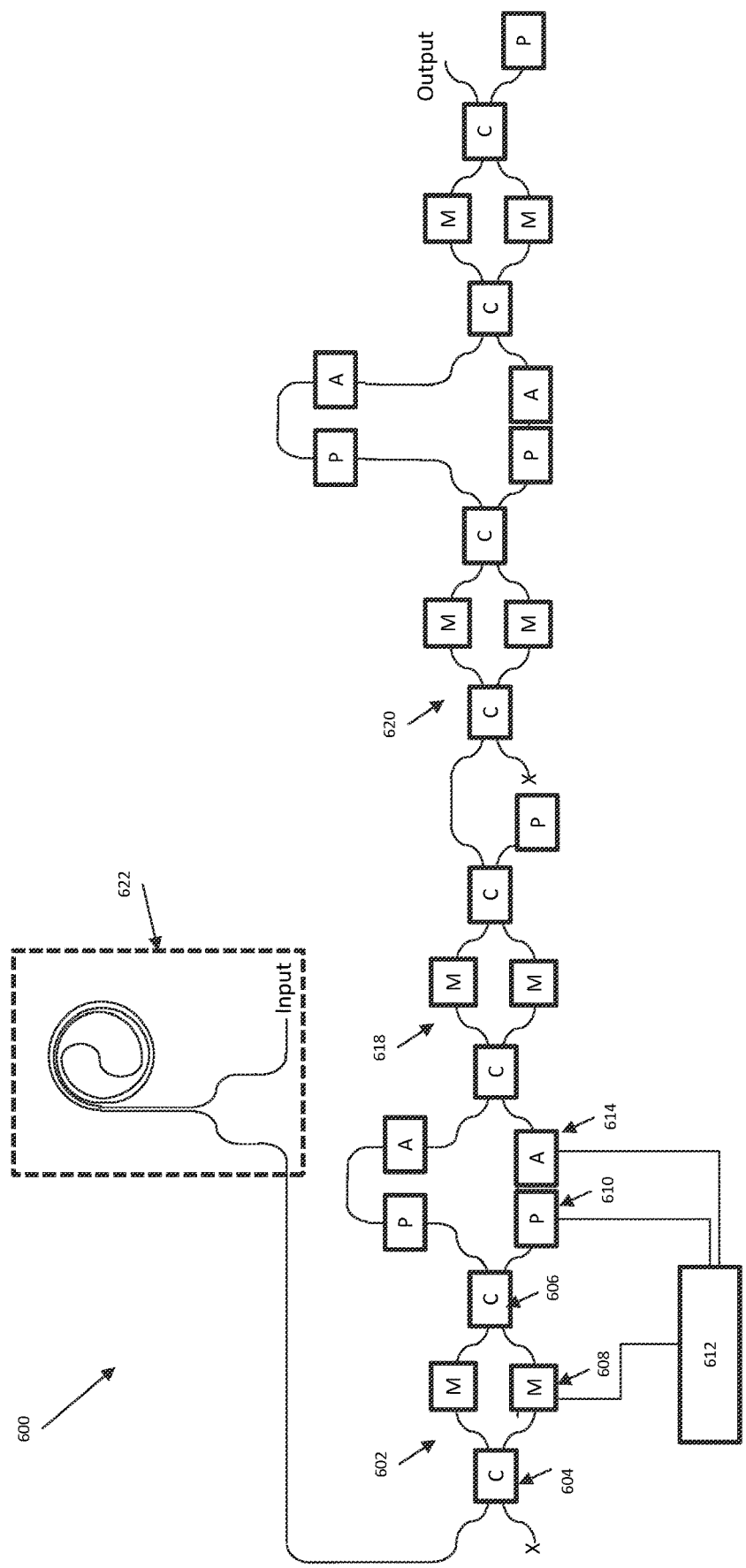
FIG. 6 illustrates an embodiment of a variable delay module including a Mach Zehnder switches with couplers, modulators and optional controllable loss devices between each stage, and optional power monitors of the present teaching.

FIG. 6 illustrates an embodiment of a variable delay module 600 including Mach Zehnder switches 602, 618, 620 with couplers 604, 606, C, and modulators 608, M, and optional controllable loss devices 614, A, between each stage, and optional power monitors 610, P of the present teaching. One or more of the attenuators 614, A, power monitors 610, P, and modulators 608, M, can be monitored and controlled by a controller 612. This variable delay module 600 embodiment also includes a 2:1 switch 618 and 1:2 switch 620 cascaded between the delay stages as presented, for example, in the embodiments of VDL modules 400, 500 FIGS. 4 and 5. A Mach-Zehnder-switch-based module 600 with cascaded switches 618, 612 between delay stages can even further significantly increase the multipath extinction as compared, for example, to the embodiments of delay modules 400, 500 of FIGS. 4 and 5. The variable delay module 600 uses, instead of one stage of 2×2 switching, a cascade of a 2:1 switch 618 and a 1:2 switch 620 one or more of each intermediate node. While only two stages of delay are shown for simplicity, the extension to more delay stages is clear to those skilled in the art. This cascaded switches 618, 620 approach extinguishes the light in the undesired arm from traveling into the next switch. This approach can be used with or without the absorptive devices 516, A, in one or more of the delay stages.

Also shown in the dotted box 622 of FIG. 6 is one example of a tightly confined wave routing option, a spiraled waveguide. This and other known methods to provide a long optical delay in a compact package can be used to add delay at an input to the variable delay module 600, which is the configuration shown. More generally, this kind of long delay can be included in any path or at the output of a module. This dashed box 622 version is shown as an input stage to the switch as will be described below, but each of the long arms of the switch could contain a tightly confined waveguide pattern. Many other possibilities to a spiral design exist to get the maximum delay in a small amount of PIC wafer real-estate, such as raster shape and other patterns.

Embodiments of the variable delay line modules of the present teaching may use other types of switch structures than Mach-Zehnder switches. The switches in various embodiments can be integrated into photonic integrated circuits. Switches that can be advantageously integrated include, for example, MEMS actuated coupler-based switches, electrooptical or thermally driven directional couplers, micro-ring resonator (MRR) switches, and broadcast and select based switches. MRR switches have a challenge that they are harder to make broad optical bandwidth if their resonance is too narrow, and so this is a consideration for these embodiments. Embodiments using broadcast and select based switches are described further below.

Figure 7:
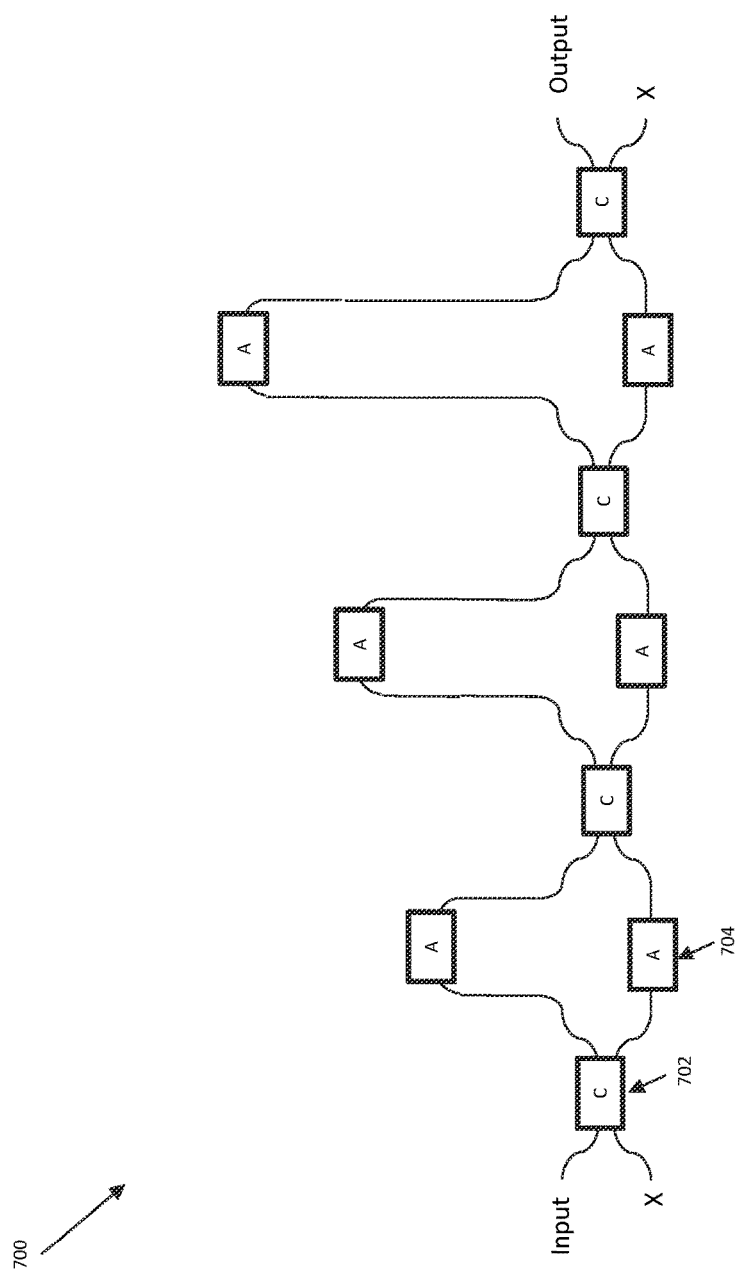
FIG. 7 illustrates an embodiment of a variable delay module including beam splitters/combiners with controllable loss devices in the arms between stages of the present teaching.

Some embodiments of the present teaching use a controllable absorptive loss in each arm of each switch stage with no switches and a 2×2 optical coupler instead. FIG. 7 illustrates an embodiment of a variable delay module 700 including beam splitters/combiners 702 with controllable loss devices 704 in the arms between stages of the present teaching. Variable delay module 700 has the advantage of not having the associated complexity to control a Mach Zehnder switch. Variable delay module 700 has a disadvantage as compared to Mach Zehnder switch-based embodiments that is has over 3 dB of loss at each switch stage. For an 8-stage switch, that can be in excess of 24 dB loss for the variable delay module 700. In operation, light is coupled into the first 50/50 coupler 702, C. Each output arm of the coupler 702, C, has a controllable attenuator 704, A, that can be set for maximum or minimum attenuation depending on the desired delay of the stage. Thus, in these embodiments, rather than a switch state setting an optical path through the variable delay module, the controlled attenuation sets the desired optical path, and thus determines the desired delay provided by the variable delay line module. The elements of the variable delay module 700, including any or all of inputs and outputs, couplers 702, C, and controllable attenuation devices 704, A, can be integrated onto one or more PICS.

As loss is important even if the VDL is located in the reference arm it is important to still minimize loss and scattering. As such low loss PIC materials such as Silicon Nitride can be used which has the advantage of being able to operate over a broad optical window and even without electrooptical activation of the phase modulators one can use thermal tuning for lower loss and higher wafer yield which still can have relatively fast response times. There are many other materials such as silicon on insulator, InP, GaAs, PLC, that can be used to construct the coherent receiver, the VDL, and the many of the other structures shown in FIGS. 2A and 2B.

As mentioned above it can be important to have a small VDL step size. The example cited above was during intravascular or endoscopic pullback helical scan 3D imaging, stretching or heating or other environmental effects can lead to degradations in image quality as the imaging information can look like the sample is moving during pullback when in fact it is an artifact of the optical path from the laser to the sample and back to the receiver that is varying. A traditional solution is to have a fluidical such as the slight reflection from the inner or outer distal sheath or window of the catheter when light exits the catheter toward the sample, and track that fluidical to keep it at the same place on the image as the pullback procedure is performed. If the minimal step size of the VDL is sufficiently fine (e.g. a small number) then that is a satisfactory solution. But for high quality images that minimum step size can in some applications be lower than 10 μm (or comparable to the axial resolution of the OCT system). To achieve 10-μm minimum step size and 25-mm maximum step size would require ~12 stages. While the number of stages can be increased to achieve a desired maximum step size, it comes at a cost of requiring more real-estate on the PIC die. This can result in increased optical loss, increased multipath (especially in the measurement range window), fabrication yield concerns and other factors.

As mentioned earlier, one approach to get a finer step size is to have one of the stages of the VDL be a thermally controlled tightly spiraled patterned, raster pattern or other tightly confined pattern to create long waveguide. Using a tightly confined waveguide pattern, in place of one of stages of the multi stage Mach Zehnder is one embodiment that allows very small (practically zero) minimum step (at no thermally activation or cooling) to the maximum path length expansion provided by the maximum thermally activation heating, while using minimum wafer real-estate and allowing the thermal region and heaters to be confined. This is conceptually shown in the dotted box of FIG. 6 illustrating a spiral waveguide could be used at the input (or the output or any switch stage) of VDL 600 (thermal or electrooptical control is not shown). (It is also possible that the thermally control tightly spiraled waveguide could be in one or more arms of the switches but that has disadvantages in total possible delay and other complexities). An example of an 8-stage VDL with ~25 mm total delay and 0.1 mm minimum delay increment is described herein. In another embodiment, if the first stage of the VDL includes a thermally (or electrooptically) activated variable delay long waveguide in low loss silicon nitride or other suitable material, then a variable delay of 0 to ~0.5 mm or more is achievable and the number of total stages can be reduced. This also has the advantage that during measurements say in a cardiovascular helical scan pullback imaging (or other applications) that the delay can be continuously adjusted vs. the discrete adjustment that happens when a switch state is changed. A change in the switch state can degrade the image if the switch is not fast (or occurs during blanking period) compared to the smooth continuous change in a thermally or electronically activated spiral waveguide. The discrete delay modules can produce dropouts of the OCT measurement signal during a period when an optical path from the input to the output of the variable delay line is selected, and this is avoided by use of a continuous delay adjustment that can be achieved either by thermal tuning of a long-delay waveguide and/or electronic delay as described herein.

An alternative is to have a virtual in electronic hardware and/or software VDL and a physical photonic VDL and blend the two solutions. This can be accomplished as follows. The control and processing unit 251 of FIG. 2B controls the start of each A-scan line data collection as in known in prior art. There is a clock pulse that signifies the start of the data or each collected A-line. This line start data clock indicator is used to in many ways including creating the B-scan (or 2D) and 3D images. Tracking of a distal fluidical or other approaches to mitigate differential changes in path length that then can be used to control the VDL are also known in the prior art. It is possible to adjust that A-line start clock signal in time by adding an electronic delay and appropriate buffering and other processing within control and processing unit 201 and that has a similar effect from the perspective of the displayed image as adjusting the VDL.

One advantage of using an electronic delay of the clock is that the minimum step granularity can be quite small, at the level of an individual axial pixel (usually less than the axial resolution of the of OCT system). One disadvantage of this is that if the total measurement range desired in the tissue is say 0-7 mm then tracking the path lengths electronically via clocks will eat into that range. If the electronic delay is adjusted over 0-1 mm then the actual tissue measurement could be 0-6 mm in some cases. One embodiment is to combine the two solutions where the fine adjustment is done using the electronic clock and the coarser adjustment is done using one of the embodiments or a combination of embodiments described above for the photonic VDL. This provides a powerful and fast and inexpensive solution to a VDL. In an alternative embodiment, the clock pulse is not shifted to create the variable delay but the A-line is adjusted longitudinally by shifting it closer or farther relative to other A-lines in an electronic buffer representing a 1D, 2D, or 3D image (e.g. B-scan). The central point is that there is an electronic, software or adjustment to the A-line instead of, or addition to, a physical adjustment to the A-line reference with respect to the longitudinal or depth dimension within the sample. The electronic and/or software adjustment to the relative delay may be referred to as an electronic VDL.

In one embodiment the entire OCT A-Scan imaging engine depicted in FIG. 2B and outlined by box 280, can be packaged in a very small footprint. By having: 1) some or all of the items shown within the dashed line, 277, of FIG. 2B on one or a few photonic integrated circuits mounted on a substrate(s), (e.g. one or more of beam splitters/combiners, polarization beam splitters/combiners, optical hybrids, k-clock, power monitors, polarization controller, a variable optical delay line, and integrated photodetectors); 2) mounted in close proximity on the same or an adjacent substrate is a FPGA, ASIC, and/or other electronics; and 3) a swept source laser mounted on the same or an adjacent substrate an ultra-small footprint, low weight, and low cost package is possible and that package can even be pluggable.

Figure 8:
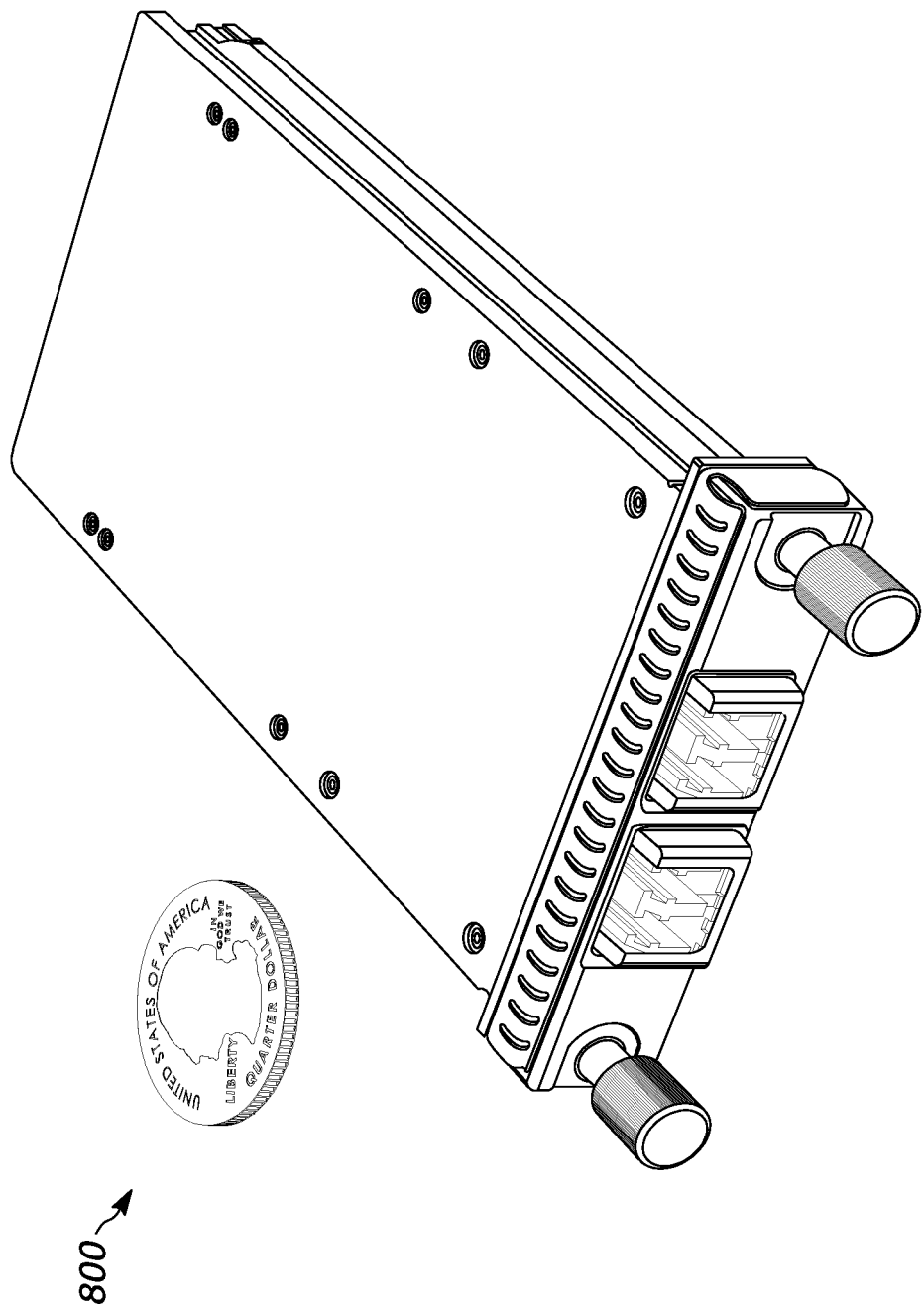
FIG. 8 illustrates an embodiment of a small pluggable OCT imaging engine of the present teaching.

One feature of the present teaching is the recognition that imaging engines can be implemented in pluggable modules. FIG. 8 illustrates an embodiment of a small pluggable OCT imaging engine 800 of the present teaching. Pluggable transceivers are common place in fiber optical telecommunications and data communications but have never been possible in things like OCT imaging engines. Another important feature of the present teaching is that by incorporating the variable delay line and/or other items, a small and convenient pluggable package is possible and will yield large benefits for system integrators to rapidly be able to integrate OCT into their products, perform maintenance, and upgrades, and provide other benefits. The pluggable engine 800 embodiment of FIG. 8 shows two duplex pair of fiber optical connectors. One connector is for the two links that provide for the sample path and the other connector is for the reference arm patch cord. These are symbolized in FIG. 2B by the small squares on the right edge of box depicting the engine 280. It is also possible that one of the external facing duplex connectors can be eliminated and path 266 is contained inside the pluggable unit shown in FIG. 8. On the other end of the unit is an electrical connector to provide input and output digital and/or analog signals to the customer equipment as well as the high-speed A-scan imaging data. Such signals could include, for example: sweep enable/disable, sweep frequency waveform, sweep power waveform, polarization waveform, l crossing references, output optical power monitor, reference power monitor, photodetector photocurrent monitors, FFT & scan conversion, buffering, framing. clocking, arbitrary function generator, customer control interface (e.g. USB/Ethernet,) customer data Interface (e.g. PCIe, Ethernet, etc.), and power supplies.

In prior art OCT and other interferometric imaging, sensing, and ranging systems, the range over which high resolution depth information can be obtained is often limited. For example, in commercial ophthalmic and cardiovascular OCT systems, the depth scanning range is typically less than 10 mm from the surface of the tissue to the maximum imaging depth. In conventional SS-OCT systems, the depths are limited by the fact that high depth information is encoded in high beat (or i.f.) frequencies in the electrical signal from the photodetectors. The electrical receiver chain has limited electrical bandwidth in the photodetectors, TIA, AGC, and ADC elements. Another limitation on imaging depth is the signal strength in samples, such as highly scattering human tissue like the retina, or skin, or coronary artery decays quite quickly with depth and there is limited SNR once the light penetrates more than 3-5 mm in highly scattering tissues or samples. SD-OCT systems have analogous depth limitations. However, in some applications, additional depth information is highly desirable. For example, if the contours of the specimen are large (e.g. microscope guidance of a surgical area, or imaging a human hand or face, or imaging a moderately large 3D printed object), then the OCT system will quickly run out of its window of operation if it can only image 0-10 mm.

When the OCT light is passing through air, there is little attenuation with properly design optical imaging lenses (e.g. with proper Rayleigh range, beam waist parameters). To increase axial measurement range, it is possible with the integrated photonic VDL described here to track the surface of the specimen by adjusting or tracking (in an automated or manual way) the VDL to keep the OCT signal within its imaging range.

Figure 9:
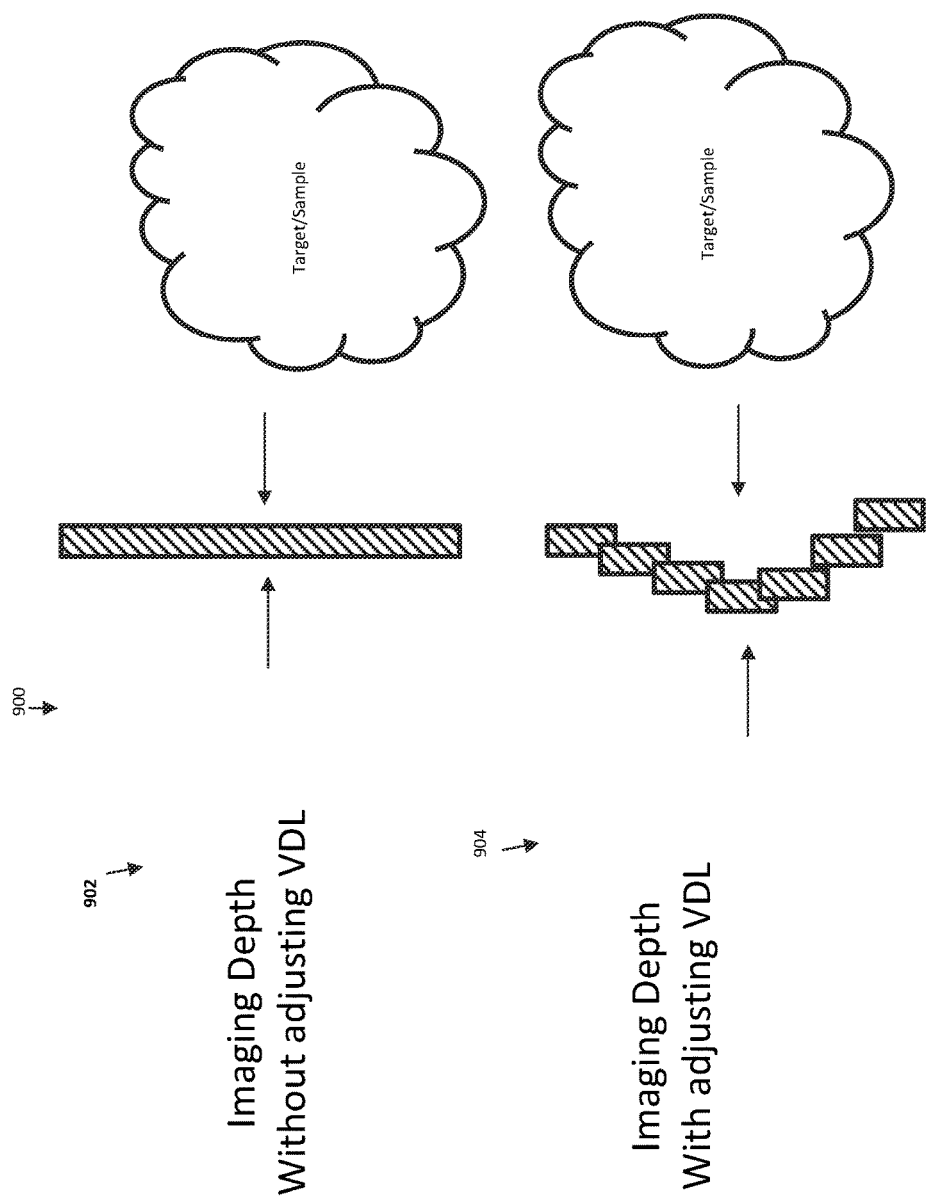
FIG. 9 illustrates diagrams that illustrate the concept of allowing increased imaging depth by actively tracking or adjusting a Variable Delay Line (VDL).

Because the VDL approach described here can be compact, low-cost, and relatively fast, this combination of keeping the region of interest of the OCT signal near the surface of a large object being imaged by automatically adjusting the VDL can allow for much larger imaging depth than 0-10 mm of conventional OCT systems without sacrificing high resolution. This concept is schematically shown in FIG. 9. FIG. 9 illustrates diagrams 900 that illustrate the concept of allowing increased imaging depth by actively tracking or adjusting the VDL. In the top section diagram 902, a b-scan imaging area without adjusting the VDL during the scan is shown and the depth of the OCT image is illustrated by the two arrows. On the bottom section diagram 904, the OCT imaging area is shown with the ability to adjust the VDL. The diagram indicates that even though the OCT imaging depth is not increased once the light hits the surface of the target, a larger region can be scanned by tracking the surface using the OCT signal and adjusting the VDL to keep the image within the OCT imaging depth. This approach of auto tracking is similar to the tracking of the fiducial in the intravascular OCT example described herein but, much large displacements are possible with the integrated photonic VDL describe here and this can be useful in many applications including applications, such as 3D printing where large object can be printed and both contour and depth information is useful.

EQUIVALENTS

While the Applicant's teaching is described in conjunction with various embodiments, it is not intended that the Applicant's teaching be limited to such embodiments. On the contrary, the Applicant's teaching encompasses various alternatives, modifications, and equivalents, as will be appreciated by those of skill in the art, which may be made therein without departing from the spirit and scope of the teaching.

What is claimed is:

1. An interferometric measurement system comprising:
    a) a first optical port configured to receive an optical signal from an optical source;
    b) a second optical port configured to receive an optical signal from a target;
    c) a photonic integrated circuit having an input coupled to the first optical port, the photonic integrated circuit comprising variable delay configured to select between at least two optical paths from the input of the photonic integrated circuit to a first input of an optical receiver such that the optical signal from the optical source provided to the input of the photonic integrated circuit and passing to the first input of the optical receiver experiences an optical delay based on a selected one of the at least two optical paths;
    d) an external optical path optically coupled to the photonic integrated circuit such that the optical signal from the optical source is coupled to the first input of the optical receiver through a reference path that contains the variable delay and the external optical path;
    e) the optical receiver further comprising a second optical input coupled to the second optical port, the optical receiver configured to receive the optical signal from the target and to receive the optical signal from the optical source that experiences the optical delay based on the selected one of the at least two optical paths and a delay from the external optical path and to generate a corresponding electrical receive signal at an electrical output; and
    f) a processor having an electrical input connected to the electrical output of the optical receiver, the processor configured to generate at an output an interferometric measurement signal based on the electrical receive signal.

2. The interferometric measurement system of claim 1 wherein the variable delay is further configured such that a leakage signal from the input to the output of the variable delay is less than a desired value.

3. The interferometric measurement system of claim 2 wherein the desired value is less than −50 dB.

4. The interferometric measurement system of claim 1 wherein the variable delay comprises a stepped-stage variable delay.

5. The interferometric measurement system of claim 4 wherein the stepped-stage variable delay comprises a cascade of two Mach-Zehnder interferometric modulators.

6. The interferometric measurement system of claim 4 wherein the stepped-stage variable delay comprises a cascade of three Mach-Zehnder interferometric modulators.

7. The interferometric measurement system of claim 1 wherein the variable delay comprises at least one attenuator configured to reduce optical leakage.

8. The interferometric measurement system of claim 7 wherein the at least one attenuator comprises an active attenuator.

9. The interferometric measurement system of claim 1 wherein the variable delay is further configured to select between at least two optical paths from the input to the output continuously.

10. The interferometric measurement system of claim 1 wherein the variable delay is further configured to select between at least two optical paths from the input to the output in discrete steps.

11. The interferometric measurement system of claim 1 wherein the variable delay is further configured to operate in a single polarization.

12. The interferometric measurement system of claim 1 wherein the variable delay is further configured with at least one optical path having a spiral shape.

13. The interferometric measurement system of claim 1 wherein the variable delay is further configured with at least one optical path having a raster pattern shape.

14. The interferometric measurement system of claim 1 wherein the variable delay has optical waveguides designed for minimal chromatic dispersion.

15. The interferometric measurement system of claim 1 wherein the processor is further configured to add electronic delay to the receive signal.

16. The interferometric measurement system of claim 1 wherein the processor is further configured to compensate for a chromatic dispersion in the variable delay.

17. The interferometric measurement system of claim 16 wherein the compensation for chromatic dispersion is performed in real time.

18. The interferometric measurement system of claim 16 wherein at least some of the compensation for chromatic dispersion is predetermined.

19. The interferometric measurement system of claim 1 wherein the processor is further configured to generate an optical coherence tomography (OCT) measurement signal.

20. The interferometric measurement system of claim 19 wherein the OCT measurement signal has an image depth that corresponds to the optical delay based on the selected one of the at least two optical paths.

21. The interferometric measurement system of claim 19 wherein the processor is further configured to generate a continuous electronic delay that prevents a dropout of the OCT measurement signal during a period when an optical path from the input to the output of the variable delay is selected.

22. The interferometric measurement system of claim 1 wherein the photonic integrated circuit comprising the variable delay further comprises the optical receiver.

23. The interferometric measurement system of claim 1 further comprising the optical source.

24. The interferometric measurement system of claim 23 wherein the photonic integrated circuit comprising the variable delay further comprises the optical source.

25. The interferometric measurement system of claim 1 further comprising a polarization controller having an input coupled to the first optical port and an output coupled to the input of the variable delay.

26. The interferometric measurement system of claim 25 wherein the photonic integrated circuit comprising the variable delay further comprises the polarization controller.

27. The interferometric measurement system of claim 25 wherein the variable delay is configured to operate on a single polarization.

28. The interferometric measurement system of claim 1 wherein the variable delay is further configured such that a loss of the optical signal from the optical source provided to the input and passing to the output is nominally the same for each of the at least two optical paths.

29. The interferometric measurement system of claim 1 wherein the external optical path comprises an external fiber path.

30. The interferometric measurement system of claim 1 wherein the variable delay is further configured to select between at least two optical paths from the input to the output continuously and in discrete steps.

31. The interferometric measurement system of claim 1 further comprising a polarization controller having an input coupled to the first optical port.

* * * * *